United States Patent
Gordin et al.

(10) Patent No.: US 8,651,704 B1
(45) Date of Patent: Feb. 18, 2014

(54) SOLID STATE LIGHT FIXTURE WITH COOLING SYSTEM WITH HEAT REJECTION MANAGEMENT

(75) Inventors: Myron Gordin, Oskaloosa, IA (US); Joe P. Crookham, Oskaloosa, IA (US)

(73) Assignee: Musco Corporation, Oskaloosa, IA (US)

( * ) Notice: Subject to any disclaimer, the term of this patent is extended or adjusted under 35 U.S.C. 154(b) by 1029 days.

(21) Appl. No.: 12/623,875

(22) Filed: Nov. 23, 2009

Related U.S. Application Data

(60) Provisional application No. 61/120,151, filed on Dec. 5, 2008.

(51) Int. Cl.
*F21V 29/00* (2006.01)

(52) U.S. Cl.
USPC .................. 362/294; 362/145; 362/373

(58) Field of Classification Search
USPC ............... 362/145, 147, 149, 218, 294, 373
See application file for complete search history.

(56) References Cited

U.S. PATENT DOCUMENTS

| | | |
|---|---|---|
| 3,818,486 A | 6/1974 | Bailey |
| 3,828,180 A | 8/1974 | Meckler |
| 3,926,106 A | 12/1975 | Deusing et al. |
| 3,933,678 A | 1/1976 | Graham |
| 3,986,018 A | 10/1976 | Ishii |
| 4,081,023 A | 3/1978 | Edelstein et al. |
| 4,204,572 A | 5/1980 | Wikstrom |
| 4,774,643 A | 9/1988 | McGinnis et al. |
| 5,083,194 A | 1/1992 | Bartilson |
| 5,162,906 A | 11/1992 | Yorita et al. |
| 5,173,839 A | 12/1992 | Metz, Jr. |
| 5,255,322 A | 10/1993 | Farinelli et al. |
| 5,884,114 A | 3/1999 | Iwasaki |
| 6,101,819 A | 8/2000 | Onaka et al. |
| 6,229,507 B1 | 5/2001 | Nakamura et al. |

(Continued)

FOREIGN PATENT DOCUMENTS

| | | |
|---|---|---|
| WO | WO 91/11024 A1 | 7/1991 |
| WO | WO 03/096387 A2 | 11/2003 |

(Continued)

OTHER PUBLICATIONS

Aegis Intelligent—IR, Derwent Systems Ltd., 2007, brochure.

(Continued)

*Primary Examiner* — Y My Quach Lee
(74) *Attorney, Agent, or Firm* — McKee, Voorhees & Sease, P.L.C.

(57) ABSTRACT

Systems and methods for solid-state light source heat management are provided. A solid-state light source, e.g. having one or more LEDs, can be mounted within an enclosure. In some embodiments, a heat sink associated with semiconductor material and/or power electronics can be placed on a separate side of the enclosure that is thermally insulated or separated from the state-light source. The enclosure can include a first side or portion that allows light from the solid-state-light source (e.g., LEDs) to pass through to a target area. A fluid transfer conduit may be connected to the second side or portion of the enclosure for passing a fluid (e.g., air, water, coolant, etc.) across the heat sink to transport heat generated by the power electronics and/or semiconductor material away. The heated fluid can then be routed to, as examples, an HVAC system, a vent, water heating systems, heat exchanger systems, and/or storage systems (e.g., batteries).

14 Claims, 31 Drawing Sheets

(56) References Cited

U.S. PATENT DOCUMENTS

| | | | |
|---|---|---|---|
| 6,268,458 B1 | 7/2001 | Soane et al. |
| 6,331,109 B1 | 12/2001 | Paikert et al. |
| 6,369,411 B2 | 4/2002 | Matsumoto |
| 6,418,016 B1 | 7/2002 | Chiriac et al. |
| 6,501,103 B1 | 12/2002 | Jory et al. |
| 6,517,218 B2 | 2/2003 | Hochstein |
| 6,525,936 B2 | 2/2003 | Beitelmal et al. |
| 6,529,377 B1 | 3/2003 | Nelson et al. |
| 6,648,495 B1 | 11/2003 | Hsu |
| 6,655,823 B2 | 12/2003 | Chang |
| 6,840,662 B2 | 1/2005 | Isaacson et al. |
| 6,880,954 B2 | 4/2005 | Ollett et al. |
| 6,930,332 B2 | 8/2005 | Hashimoto et al. |
| 6,988,534 B2 | 1/2006 | Kenny et al. |
| 6,999,318 B2 | 2/2006 | Newby |
| 7,115,526 B2 | 10/2006 | Ho et al. |
| 7,204,615 B2 | 4/2007 | Arik et al. |
| 7,236,366 B2 | 6/2007 | Chen |
| 7,246,921 B2 | 7/2007 | Jacobson et al. |
| 7,251,137 B2 | 7/2007 | Iijima et al. |
| 7,307,391 B2 | 12/2007 | Shan |
| 7,318,658 B2 | 1/2008 | Wang et al. |
| 7,354,798 B2 | 4/2008 | Pogge et al. |
| 7,361,081 B2 | 4/2008 | Beitelmal et al. |
| 7,429,757 B2 | 9/2008 | Oyama et al. |
| 7,543,961 B2 | 6/2009 | Arik et al. |
| 7,548,424 B2 | 6/2009 | Altman et al. |
| 7,615,799 B2 | 11/2009 | Su |
| 7,638,808 B2 | 12/2009 | Owen et al. |
| 7,651,245 B2 | 1/2010 | Thomas et al. |
| 7,656,371 B2 | 2/2010 | Shimizu et al. |
| 7,686,469 B2 | 3/2010 | Ruud et al. |
| 7,687,753 B2 | 3/2010 | Ashdown |
| 7,798,684 B2 * | 9/2010 | Boissevain | 362/294 |
| 7,819,556 B2 | 10/2010 | Heffington et al. |
| 7,855,449 B2 | 12/2010 | De Graff et al. |
| 2002/0163001 A1 | 11/2002 | Shaddock |
| 2005/0128752 A1 | 6/2005 | Ewington et al. |
| 2006/0262544 A1 | 11/2006 | Piepgras et al. |
| 2007/0062684 A1 | 3/2007 | Turner et al. |
| 2007/0080362 A1 | 4/2007 | Scotch et al. |
| 2007/0090362 A1 | 4/2007 | Ahn et al. |
| 2007/0114010 A1 | 5/2007 | Upadhya et al. |
| 2007/0230185 A1 | 10/2007 | Shuy |
| 2008/0078524 A1 | 4/2008 | Wilcox et al. |
| 2008/0191236 A1 | 8/2008 | De Graaf et al. |
| 2008/0203412 A1 | 8/2008 | Shyu et al. |
| 2008/0212332 A1 | 9/2008 | Medinis |
| 2008/0212333 A1 * | 9/2008 | Chen | 362/373 |
| 2008/0237621 A1 | 10/2008 | Takemoto |
| 2008/0273325 A1 | 11/2008 | Wilcox et al. |
| 2009/0007978 A1 | 1/2009 | Alston et al. |
| 2009/0100702 A1 | 4/2009 | Fair |
| 2009/0161347 A1 * | 6/2009 | Teng et al. | 362/373 |
| 2010/0096993 A1 | 4/2010 | Ashdown et al. |
| 2010/0149809 A1 | 6/2010 | Ruud et al. |

FOREIGN PATENT DOCUMENTS

| | | |
|---|---|---|
| WO | WO 2005/043598 A2 | 5/2005 |
| WO | WO 2006/114726 A2 | 11/2006 |
| WO | WO 2007/044472 A2 | 4/2007 |
| WO | WO 2008/032251 A1 | 3/2008 |

OTHER PUBLICATIONS

Bush, Steve, "Lumileds Talks LED Packaging—Interview", Electronicsweekly.com, Retrieved Oct. 14, 2008 from http://www.electronicsweekly.com/Articles/2008/03/26/43394/lumileds-talks-led-packagin-interview.htm.

Ellsworth Jr., Michael and Simons, Robert, "High Powered Chip Cooling—Air and Beyond, Electronics Cooling", Retrieved Oct. 15, 2008 from http://www.electronics-cooling.com/articles/2005/2005_august_articlel.php.

Epoxies, Etc . . . , 20-3302 Water Clear Optically Transparent Epoxy datasheet.

Glynn, Colin and Murray, Darina, "Jet Impingement Cooling in Microscale", ECI International Conference on Heat Transfer and Fluid Flow in Microscale, Sep. 25, 2005.

Luxlink, "Optical Gel", Epoxy OG-1052 datasheet.

"Master Bond Application Selector Guide for Electro-Optic, Fiber-Optic Laser Applications", epoxy datasheet.

McMaye, Frank, "Electronic Packaging Characterization per JEDEC Standard, Electronics Cooling", Retrieved Jun. 24, 2009 from http://www.electronics-cooling.com/articles/1997/jan/jan96_02.php.

Philips Solid-State Lighting Solutions, "Color Kinetics Source Life Information—LED Lifetime", Retrieved Oct. 14, 2008 from http://www.colorkinetics.com/lifetime/.

Olson, Chad, "Monitoring Heat Dissipation in Electronic Systems, Power Electronics", Retrieved Jun. 25, 2009 from http://www.print-this.clickability.com/pt/cpt?expire=&title=Monitoring+Heat+Dissipation+In+Electronic+Systems+Page+of&urlID=18528715&action=cpt&partnerID=97651&fb=Y&url=http%3A%2F%2Fpower-electronics.com%2Fmag%2Fpower_monitoring_heat_dissipation%2Findex.html.

Philips Lumileds Lighting Company, "Thermal Design Using Luxeon Power Light Sources", 2006, Application Brief AB05.

ScienceDaily, "Cooling in Miniature, Without Bulky Machines, Conventional Fluids or Moving Parts", Retrieved Oct. 22, 2008, from http://www.sciencedaily.com/releases/1999/10/991027072853.htm, Cornell University.

Sofia, John, "Electrical Temperature Measurement Using Semiconductors, Electronics Cooling", Retrieved Jun. 24, 2009 from http://www.electronics-cooling.com/articles/1997/jan/jan97_03.php.

U.S. Department of Energy, "Lumen Depreciation", Retrieved Oct. 14, 2008 from http://www.netl.doe.gov/SSL/usingLeds/general_illumination_life_depreciation.htm.

Granet, Irving et al., "Thermodynamics and Heat Power", Seventh Edition, Pearson Prentice Hall, ISBN 0-13-110672-4, 1974, 8 pages.

The Unico System, "Homeowner Product Information Guide", Brochure, www.unicosystem.com, (date unknown) 4 pages.

The Unico System, "2.5" Duct with Threaded Outlet", Brochure, (date unknown), 2 pages.

Artic Cooling Freezer 7 Pro Rev.2 92mm Fluid Dynamic CPU Cooler, 2 pages, http://www.newegg.com/Product/Product.aspx?Item=N82E16835186134, [retrieved from Internet on Oct. 19, 2011].

* cited by examiner

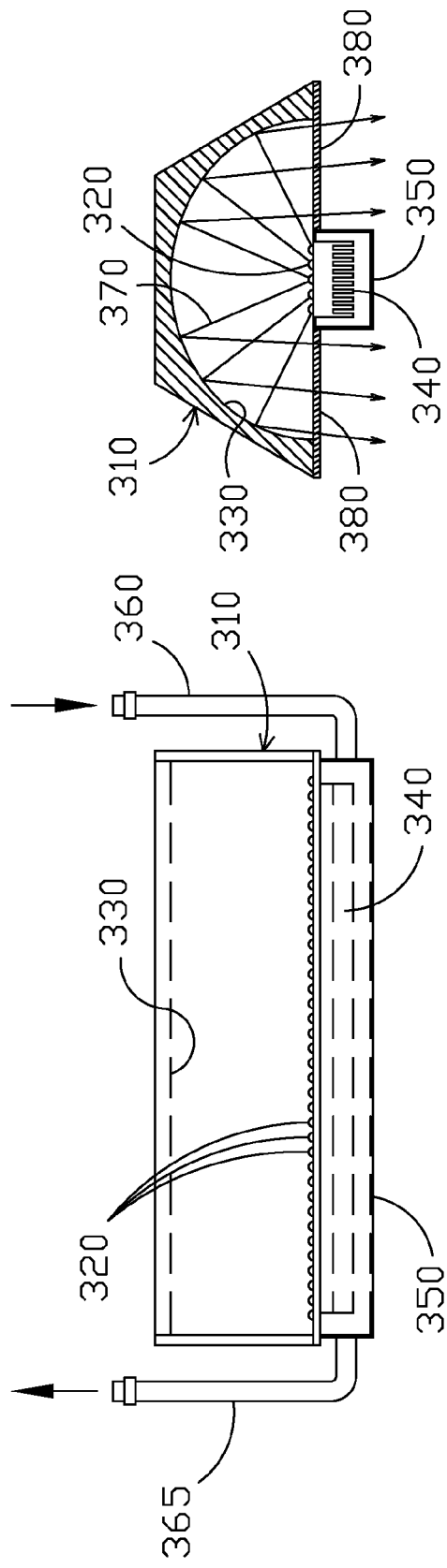

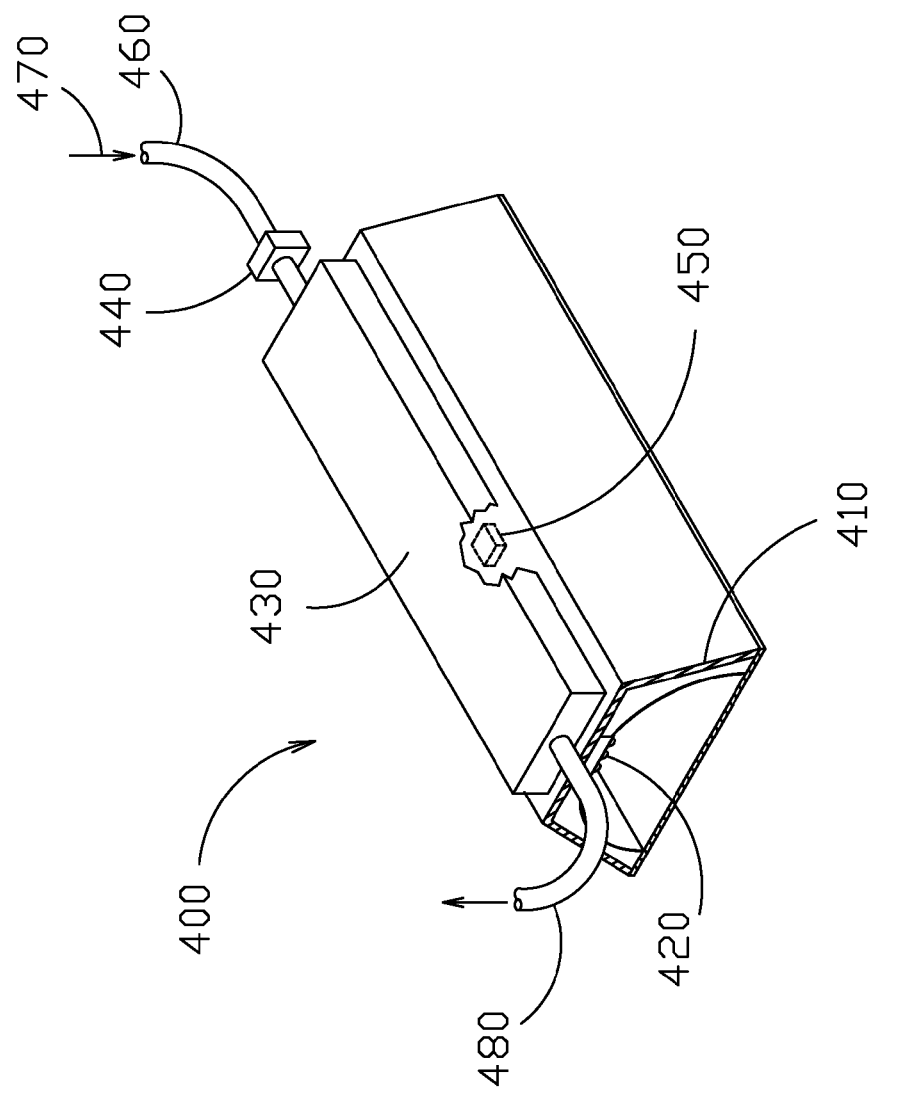

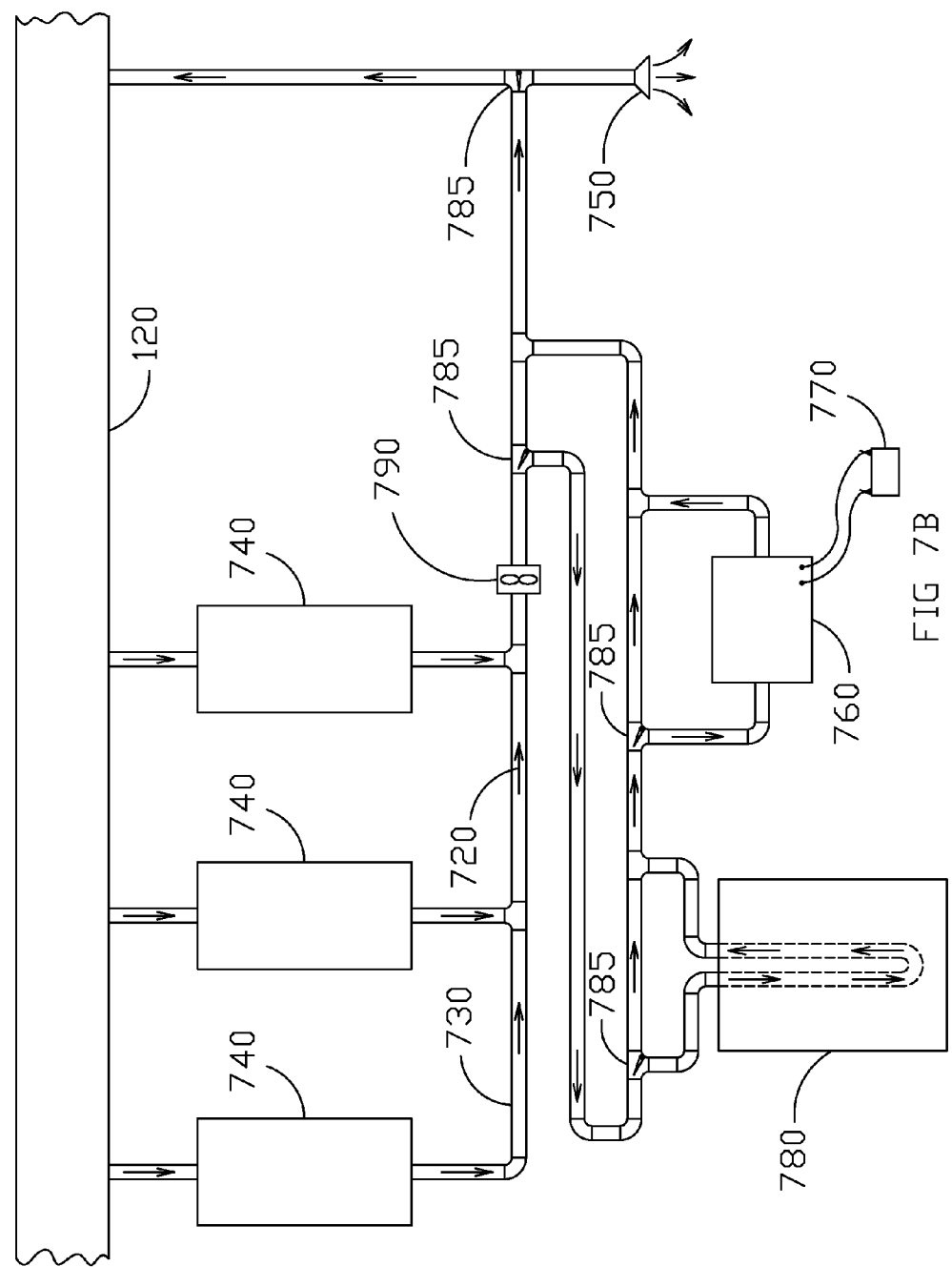

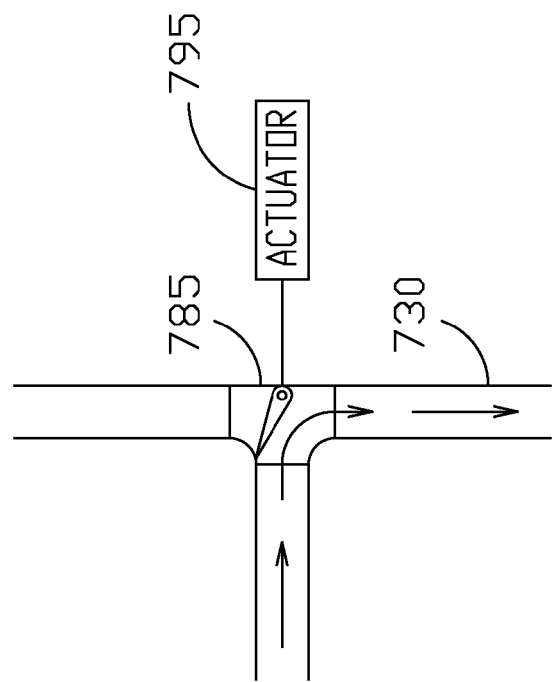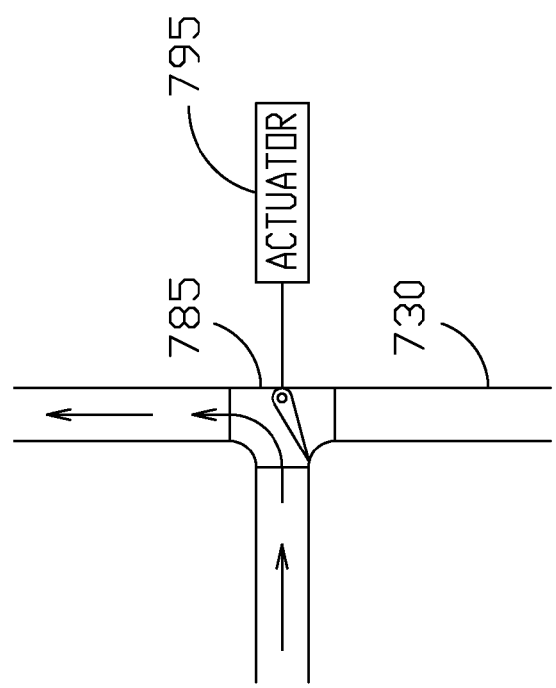
FIG 7C

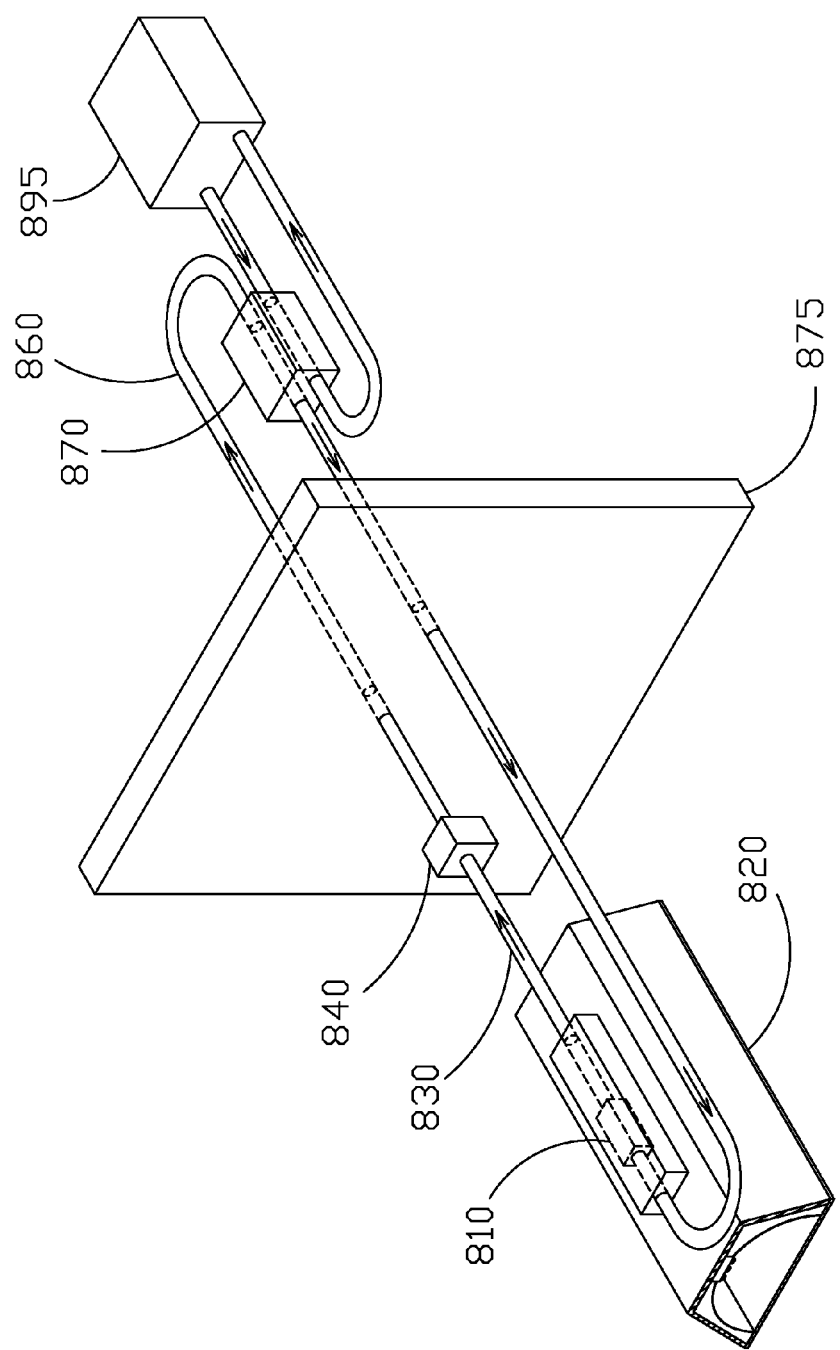

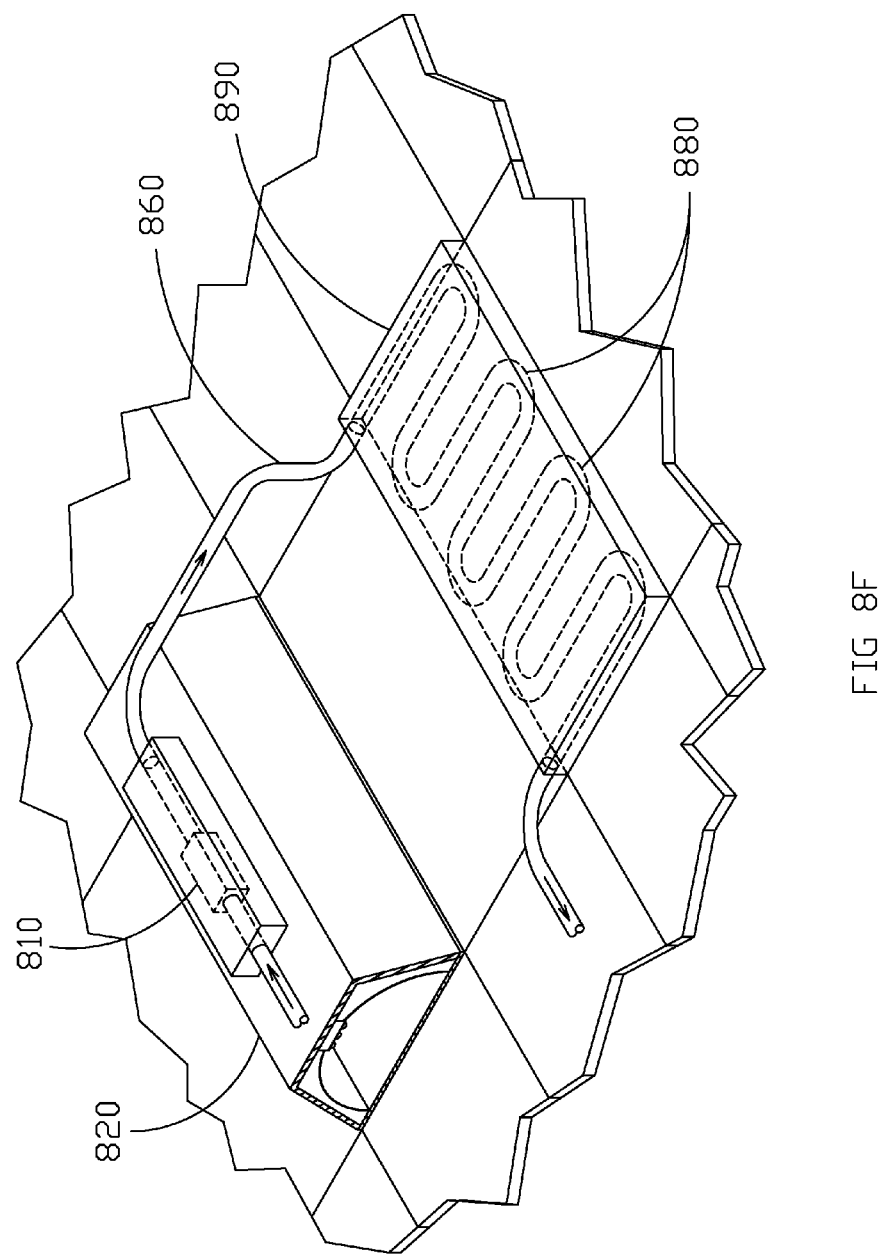

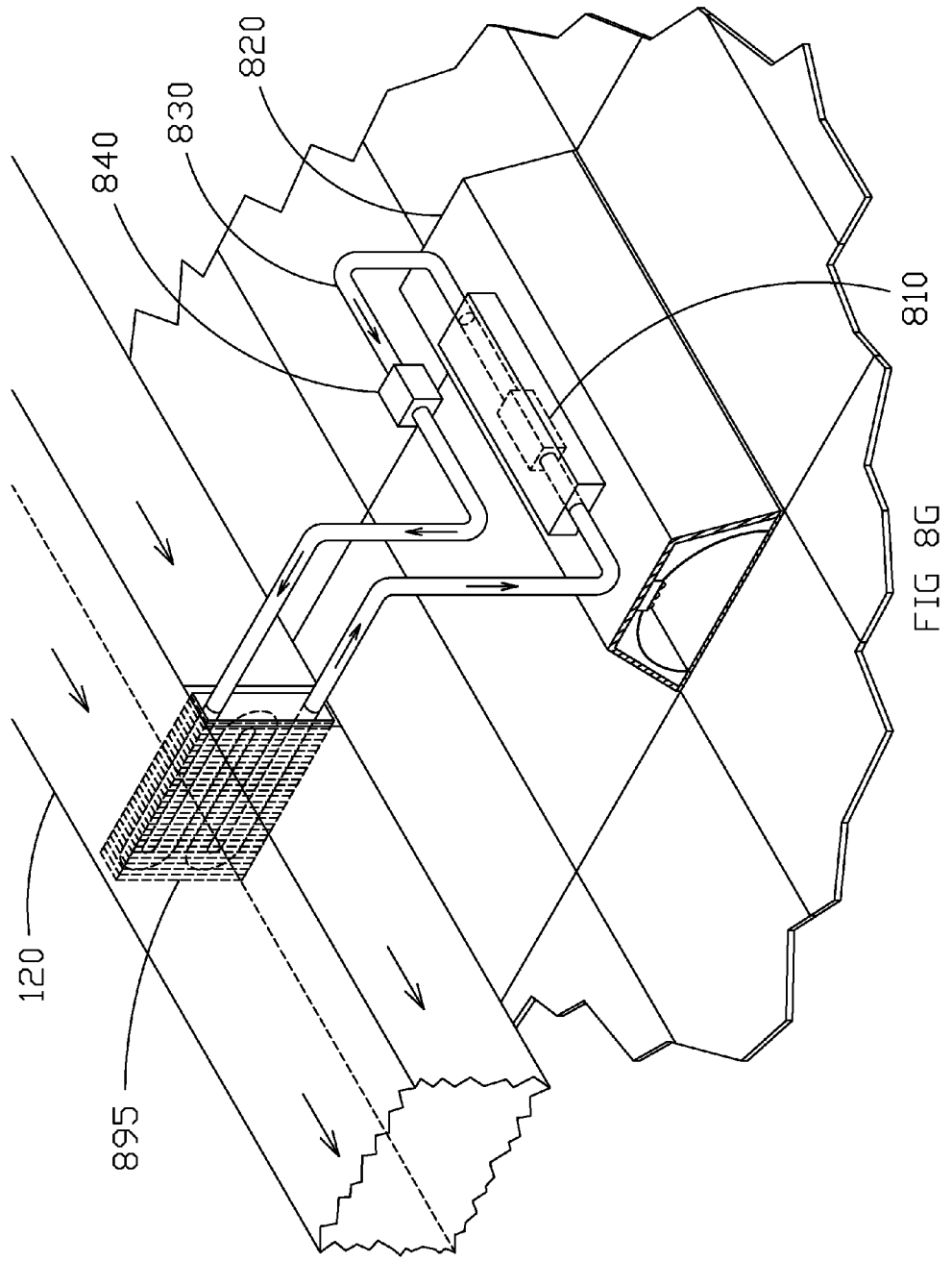

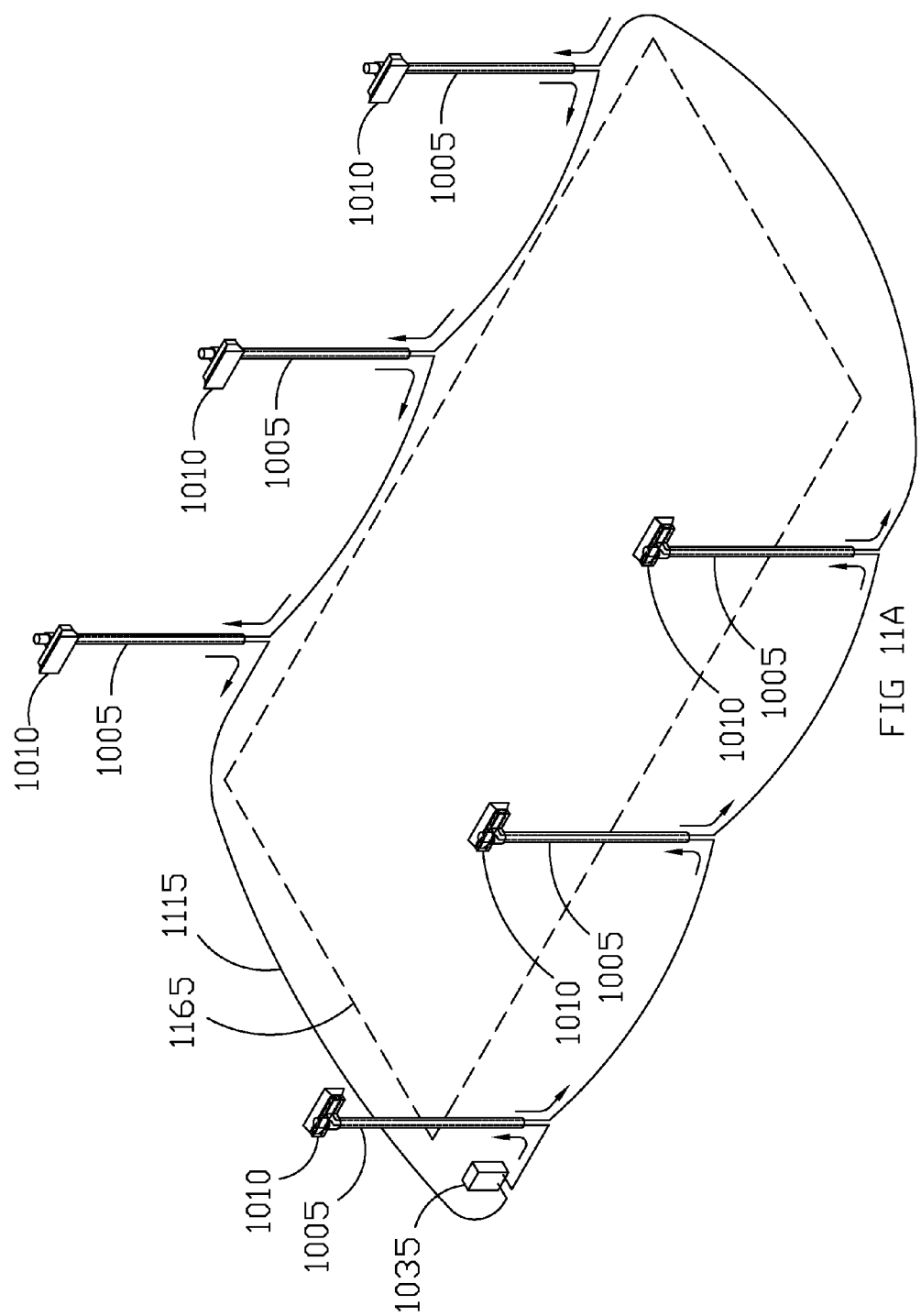

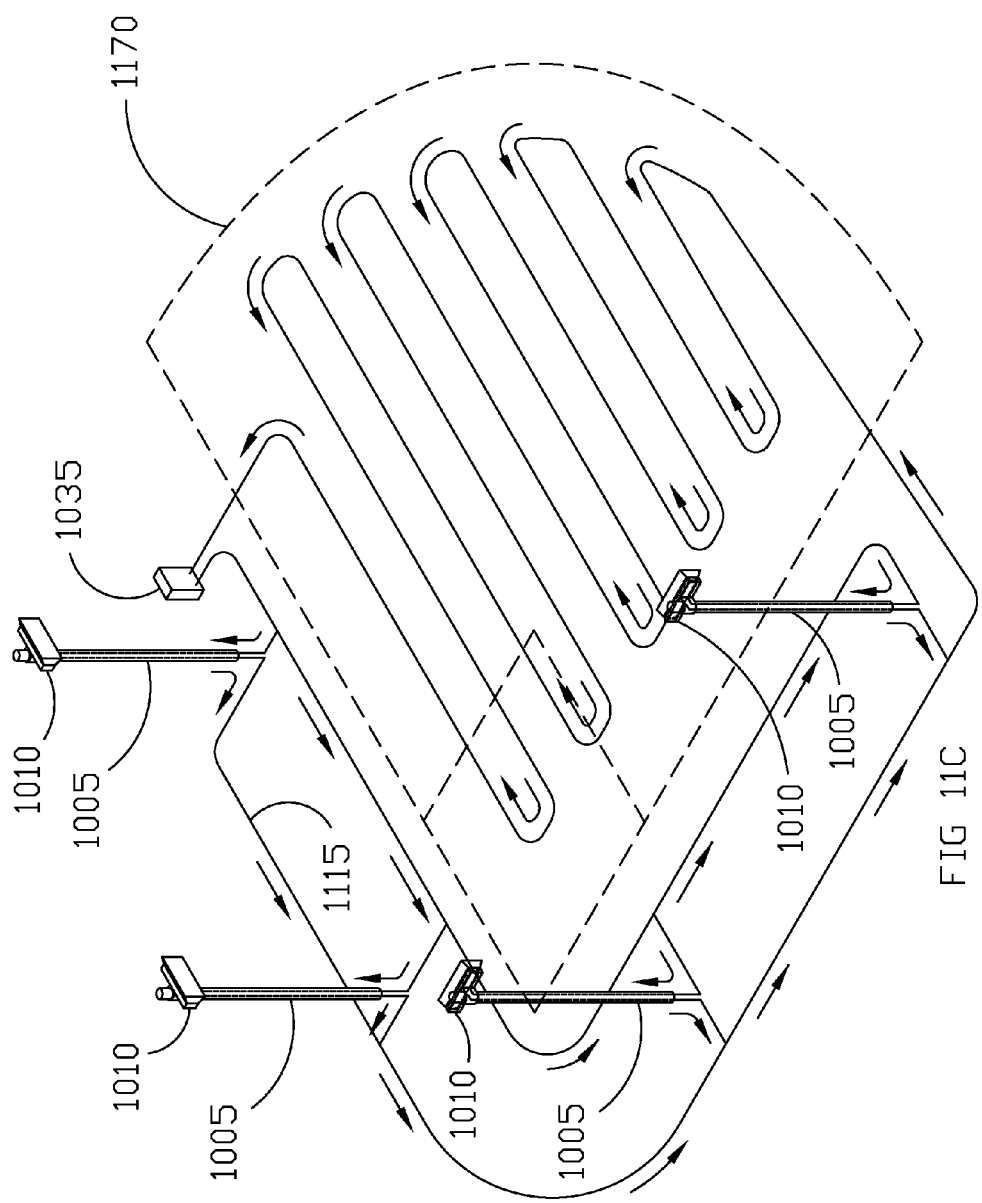

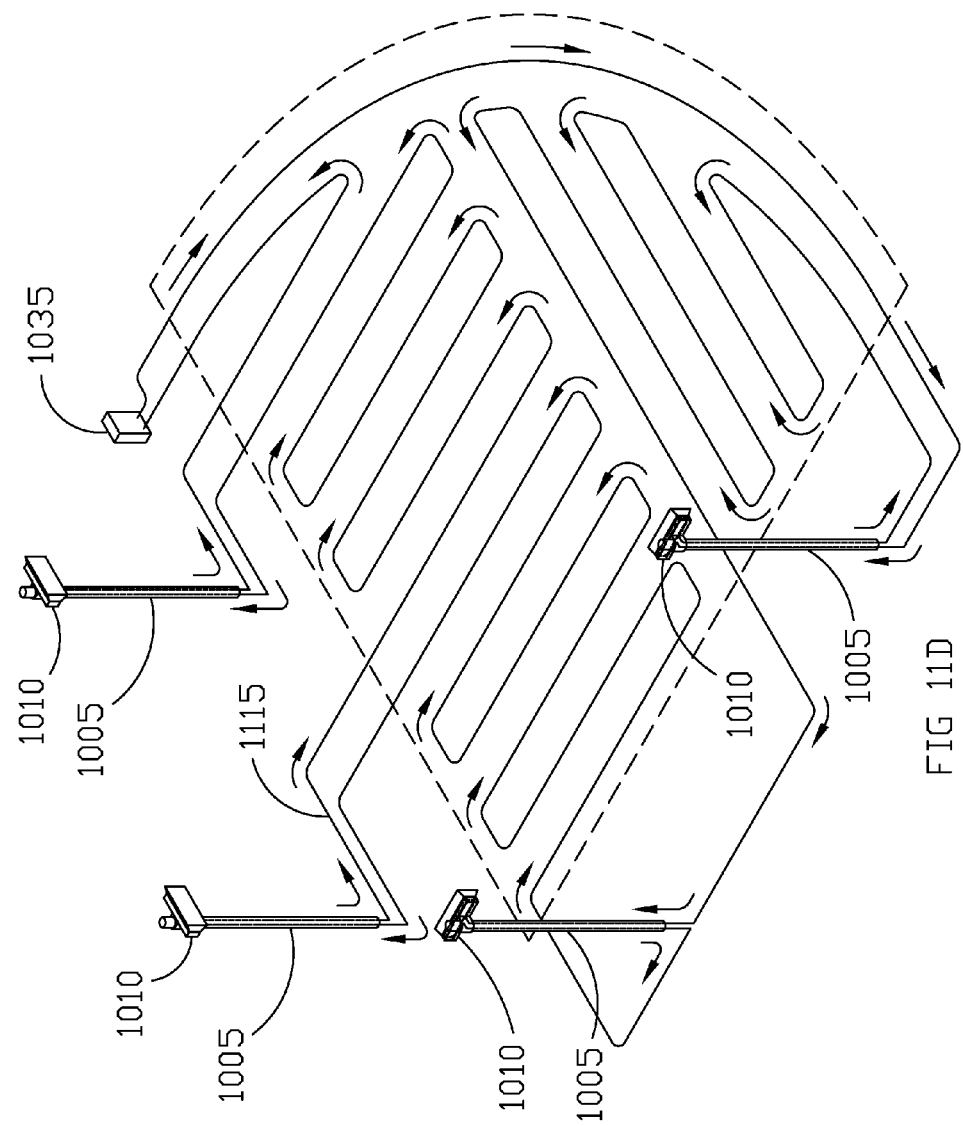

SOLID STATE LIGHT FIXTURE WITH COOLING SYSTEM WITH HEAT REJECTION MANAGEMENT

CROSS-REFERENCE TO RELATED APPLICATIONS

This application claims priority under 35 U.S.C. §119 of provisional U.S. Patent Application No. 61/120,251, filed on Dec. 5, 2008, which is hereby incorporated by reference in its entirety for all purposes.

COPYRIGHT NOTICE

Contained herein is material that is subject to copyright protection. The copyright owner has no objection to the facsimile reproduction of the patent disclosure by any person as it appears in the Patent and Trademark Office patent files or records, but otherwise reserves all rights to the copyright whatsoever. Copyright© 2008-2009 Musco Sports Lighting, Inc.

TECHNICAL FIELD

Some embodiments of the present invention generally relate to heat management systems. More specifically, some embodiments of the present invention relate to heat rejection management in LED and other solid-state lighting fixtures and devices.

BACKGROUND

The functional source of heat from an LED is primarily from what will be called the "back side" of the assembly—i.e. the location away from the "front side" where the light is emitted. This is quite unlike conventional lighting sources such as incandescent, fluorescent, high intensity discharge, which do not have this division. This division between what will sometimes also be called a "light side" (or "front side") and a "heat side" (or "back side") therefore allows a novel approach to capturing the waste heat of lighting systems in a way that is not possible with conventional lighting. Since the heat is concentrated in a location away from the "light side," the space which is illuminated by the LED can remain relatively unaffected by heat from the LED. The space on the "heat side" of the LED can be at least substantially enclosed for efficient capture of heat. Enclosing the space then allows a novel means of capturing, removing, and potentially repurposing the heat generated by LED or solid-state light operation. The term "LED" is meant to include most if not all lighting uses of light-emitting diodes (LEDs) including but not necessarily limited to semi-conductor LEDs, organic light-emitting diodes (OLEDs), or polymer light-emitting diodes (PLEDs) as sources of illumination. However, the reference to different types of LEDs is not a limitation on the scope of the invention, which is applicable to most if not all solid-state lighting (SSL), which includes the different types of LEDs (e.g., semi-conductor LEDs, OLEDs, PLEDs). SSL refers to light emitted by solid-state electroluminescence.

Buildings and other enclosed spaces are generally equipped with heating and cooling systems in order to maintain the comfort of occupants. In the summer, for example, when the temperature is warmer, the heating and cooling system will cool the building. In addition to the outside temperature, many factors can affect the temperature of an enclosed space. For example, most light fixtures produce some heat from the light source or the electrical system that provides power to the light fixture. Other electrical/electronic components such as computers and processors, lighting controllers, amplification and PA systems, etc., likewise produce heat. The heat from the light fixtures and other components is typically rejected (e.g. radiated or conducted) into the enclosed space, working against the building's cooling system. Consequently, heat from the light fixtures and other components can increase the total cost to cool the building. In addition to being expensive, the energy rejected from lighting systems and other components is usually wasted.

Therefore, an effective way to manage heat in these circumstances could be beneficial. One example could be apparatuses, methods, and systems which allow the use of LED lighting and can be highly beneficial in that they can reduce the burden on HVAC systems by concentrating and exhausting heat outside of conditioned space or directing to other beneficial uses. The embodiments outlined below can also reduce the number and/or size of LED fixtures by increasing LED lumen output.

Lighting fixtures and other electrical/electronic components can also be used in locations without climate control, such as outdoor sporting venues.

Some LEDs can emit light in the infrared (IR) wavelength(s), (e.g., at least some IR wavelength(s) alone or in combination with other wavelength(s), such as visible (VIS) or ultra violet (UV), and thus might be considered to generate heat on the "light side" or "front side" of the LED. However, at least of majority of heat from such an LED is at the "heat side" or "back side" of the LED, so the principles of the invention described herein are applicable to this type of LED also. In these types of locations, adequate heat rejection can be difficult especially when a collection of solid-state electronics is highly concentrated. Solid-state sports lights on high poles are an example of a situation in which providing adequate ambient heat sinking capability can be difficult due to the given the requirements for construction many feet in the air. Fixture size and configuration is constrained due to factors such wind loads and aesthetic considerations as well as the need to limit fixture weight to avoid excessive construction costs. This could lead to inadequate heat sinking capability or performance constraints, and potentially damage or premature failure of lighting or other electrical/electronic components. Therefore, apparatuses, methods, and systems which allow the use of LED lighting for these applications and provide effective heat management can be highly beneficial.

Examples of possible applications include, but are not limited to, illumination of indoor and outdoor spaces or areas. The principles could be applied to light generated by SSL sources for almost any application. Some additional examples include but are not limited to, illumination (including containing IR or UV wavelength(s)) for curing photosensitive materials such as in photo lithography. Other illumination or use of light applications are possible.

SUMMARY

Systems and methods are described for heat rejection management in LED and other solid-state lighting fixtures and devices. Some embodiments have application to management of heat produced by solid-state lighting fixtures (e.g., LED lighting) and systems. Some embodiments of the present invention include a solid-state light source, an enclosure, and a fluid transfer conduit. The solid-state light source, in some embodiments, can be considered a heat source which may have one or more solid-state light sources including but not limited to light-emitting diodes (LEDs) and may have power electronics which can be in various locations relative to the light sources such as LEDs including in physical contact, close proximity, or at some distance from the light source LEDs. At least a part of the heat source can be associated with a heat sink to dissipate heat generated by the heat source. The enclosure may have a plurality of walls. One wall may be at least partially transparent to allow light from the one or more LEDs to illuminate a desired target area. The solid-state light source may be mounted within the plurality of enclosure walls to divide the enclosure into two sections. The LEDs may be located in the first section facing a wall of the enclosure that is at least partially transparent. The heat sink may be located in the second section of the enclosure. The two sections may or may not be thermally insulated from one another. Alternatively, the enclosure may have a single section, having the LEDs or other solid-state light sources located on an outer mounting surface, having the "heat side" of the solid-state light source in thermal communication with the enclosure or with the mounting surface. This can be particularly beneficial in outdoors fixtures.

In some embodiments, the enclosure can include a fluid transfer conduit interface for interfacing with a fluid transfer conduit. The fluid transfer conduit allows fluid (e.g., air, gas, chilled or heated water, circulating groundwater, antifreeze solutions, refrigerant, etc.) to transport heat generated by the heat source away from the heat side or heat sink of the solid-state light source. The heat removed from the enclosure via the fluid transfer conduit may be moved by moving the fluid. Examples include but are not limited to vented from the building directly by exhausting the heated air or indirectly by means of a heat exchange method or device, supplied to one or more rooms within the building, supplied to the heating ventilation and air conditioning (HVAC) system, and/or converted to other forms of energy through use of a heat exchange method or device and/or other energy transfer systems or techniques. Other uses are possible.

The fluid transfer conduit can connect multiple solid-state light sources within individual enclosures in some embodiments of the present invention. None, some, or all of the individual enclosures may include or be operably connected or associated to one or more independently controllable fans or pumps to force the fluid across the heat sink associated with the solid-state light source housed within the enclosure.

One aspect of the invention comprises methods, apparatuses, and systems including one or more solid-state light sources, a fluid transfer method or component to bring fluid in proximity to each solid-state light source to transfer heat generated by operation of the light sources to the fluid, a method or component to move the fluid away from the light sources to either (a) manage the collected heat or (b) apply it to another location or purpose. Optionally, the heat transfer via the fluid can be from a heat sink and/or power source associated with the solid-state light sources. The heat can be optionally collected in an enclosure around at least the heat sides of the solid-state light sources. The enclosure can be thermally insulated and/or have a surface adapted to conduct heat away. The enclosure can be sealed.

Another aspect of the invention comprises a system of multiple fixtures, each fixture having one or more solid-state light sources, and a transfer method or sub-system adapted to collect heat generated in each fixture by operation of the solid-state light sources and carry or transfer it to a location for management or application. The system can efficiently and economically collect and manage source-generated heat instead of allowing the heat to radiate, convect, or conduct at or around the fixtures without organized management. Methods and systems can be designed to transfer heat in a variety of ways. Optionally, the methods and systems can be selectively combined with other systems. Examples include but are not limited to HVAC, geo-thermal, heat exchange, or energy storage.

Potential benefits of such heat management include not only collectable and beneficial use of heat. Potential benefits also include but are not limited to allowing increased operating power to the light source which can produce more light output, increased life of the light source, possible reduction of the number of light sources needed for a given lighting application, possible reduction in size, type, or function of other heat management apparatus or methods (e.g. heat sinks), possible reduction in cost or complexity of components, increase in service life, and reduction in maintenance and replacement costs, among others.

Some embodiments include a method of cooling a lighting fixture and transferring the heat to a location more or less separated from the fixture. A method according to one aspect of the invention directs that heat extracted from such a fixture can be returned to a preferred desired or instructed location within a building, can be transferred to a location outside of conditioned space in a building, or can be transferred to an energy storage system. Examples include but are not limited to electrical energy storage in batteries, thermal energy storage in stored fluid (e.g. water) or transfer to ground or thermal mass systems, or transfer to remote heat sinks.

Some embodiments include a method of cooling a lighting fixture and transferring heat from a fixture to a location more or less separated from the fixture. Some embodiments include a method of cooling a lighting fixture and reducing the heat load contribution from the fixture for an interior space that is conditioned (e.g. air conditioned, HVAC conditioned, or the like). Some embodiments include a method of cooling a lighting fixture, reducing the heat load contribution from the fixture for an interior space that is conditioned, and using the heat for useful purposes, such as e.g. heating conditioned space, conversion into other forms of energy, or recycling by heating water, etc.

Some embodiments pump fluid through the fixture to reduce the operating temperature of the light source and/or power circuits. Some embodiments pump air through the fixture to reduce the operating temperature of the light source and/or power circuits. In some embodiments, the heated air can be optionally exhausted outside the building when the air-conditioning is operating. In some embodiments, the heated air can be optionally exhausted inside the building if the extra heat is desirable. Some embodiments pump liquid through the fixture to reduce the operating temperature of the light source and/or power components.

Also envisioned are systems, methods, and apparatus which provide many benefits for solid-state lighting. These benefits can include at least some of the following: cooling a solid-state lighting fixture thereby allowing it to operate at higher wattage, reducing the size of the fixture and/or number of LEDs or other solid-state source(s), increasing lumen output; and providing benefits to an associated building or structure by managing heat generated by lighting. These benefits may be realized with lighting used in conditioned spaces by reducing the heat contribution to conditioned space; and/or if separate from HVAC system, can reduce load on cooling system due to what might be called a "concentration advantage" of more efficient transfer due to higher heat density in the envisioned enclosures, and what might be called an "isolation advantage" due to reduced conduction to associated structures; heat may be directed to a desired location such as outdoors, indoors for heating, indoors for conversion/recycling (e.g. through a heat exchanger to heat water, a thermocouple/thermopile, or peltier effect devices.

Some embodiments of the present invention provide for a method for cooling solid-state lighting fixtures. According to some embodiments, a determination can be made as to whether a HVAC unit and HVAC ductwork installed throughout a building structure are delivering heated air, cooled air, or only ventilation throughout the building structure. Fluid flow through a fluid transfer conduit positioned to carry away heat from the solid-state sources can be adjusted to increase the temperature of the fluid with heat generated by the heat source. The fluid flow can then be routed or transferred to the heated, cooled, or untreated air in the HVAC ductwork, tubing or other transport mechanism.

The envisioned embodiments have many other advantages related to the use of solid-state lighting as well. For example, certain building operation systems can benefit from better control of heat from lighting. Facilities which are sensitive to introduction of extra heat could benefit not only from the low heat rejection of LED or other solid-state lighting, but also from the ability to further isolate and extract the heat. Examples include but are not limited to walk-in coolers, freezers, scientific installations, for instance would benefit from lights which have a minimal impact on thermal loading of a room or building. Coolers and freezers could particularly benefit from using connections to existing refrigerant circuits to extract heat from solid-state light source fixtures. According to principles well known in the art, liquid phase refrigerant on what is sometimes called the 'low side' of the refrigerant cycle could be used as the coolant in the enclosure. As heat is absorbed from the fixture, refrigerant vaporizes. The refrigerant is directed by action of the system to what is sometimes called the 'high side' of the system whereupon the heat is released through condensation.

Another aspect of the invention comprises integrating a ground or thermal mass with a method and system for collecting heat generated by one or more solid-state light sources during operation. The collected heat can be dissipated in a ground or thermal mass or a remote heat sink. Alternatively, a medium used to collect the light source heat could be circulated at or near the light sources, heat from operating the light sources carried away, and that heat applied or added to another heat management system. Examples include but are not limited to ground loops, geo-thermal, and other heat or energy exchange systems.

The method and system could include monitoring, control, and switching sub-systems.

Due to the concentration of heat on the back side of the solid-state light source assembly, it is relatively easy to isolate waste heat from conditioned space. The fact that little or no IR or UV light is emitted from most solid-state lights makes them better for locations for which light in the non-visible spectrum is unwanted or harmful. Since heat is drawn directly away from the light source and not from the entire fixture housing, it does not require transfer of air through the face of the fixture housing to remove heat. Therefore, the lighting system can be a sealed system that draws air from a remote space, other than the enclosed space the fixtures might be in, thus providing benefits for any enclosure or building that requires isolation of air, control of dust, etc.

While multiple embodiments are disclosed, still other embodiments of the present invention will become apparent to those skilled in the art from the following detailed description, which shows and describes illustrative embodiments of the invention. As will be realized, the invention is capable of modifications in various aspects, all without departing from the scope of the present invention. Accordingly, the drawings and detailed description are to be regarded as illustrative in nature and not restrictive.

BRIEF DESCRIPTION OF THE DRAWINGS

Some embodiments of the present invention will be described and explained through the use of the accompanying drawings in which:

FIGS. 3A-3B illustrate examples of reflected lighting enclosures that may be used in some embodiments of the present invention;

FIG. 4 illustrates an individually controlled enclosure that may be used in accordance with some embodiments of the present invention;

FIGS. 7A-7C illustrate an example of an operating environment and components that may be used in accordance with some embodiments of the present invention may be utilized;

FIGS. 8A-8G illustrate examples of a heat exchange between LED lighting fixtures and building cooling/heating systems that use circulating fluid in accordance with some embodiments of the present invention;

FIGS. 11A-11D illustrate various examples of configurations for multiple solid-state lighting systems using circulating fluid that may be used in accordance with some embodiments of the present invention;

Figure 1:
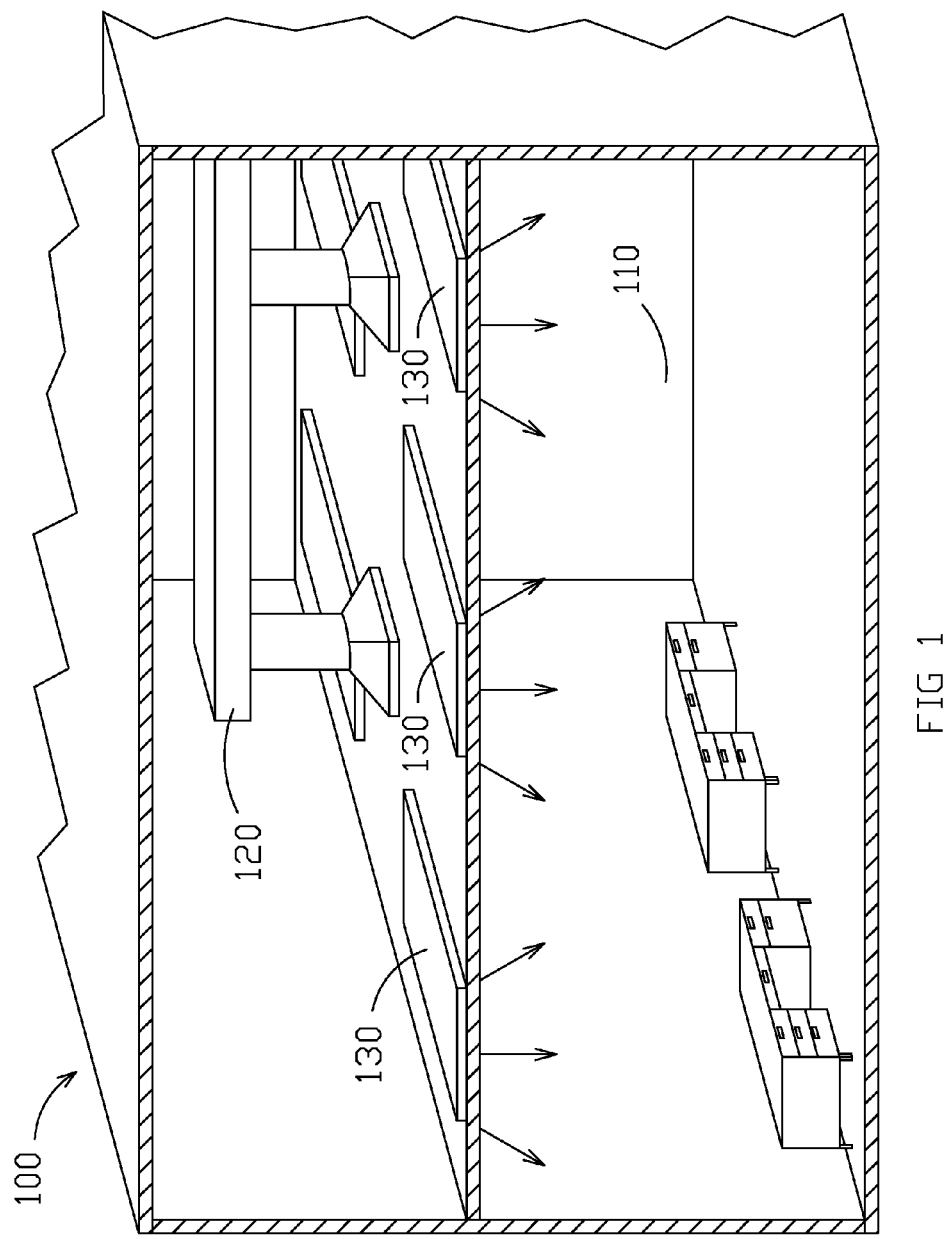
FIG. 1 illustrates an example of one operating environment in which some embodiments of the present invention may be utilized.

The drawings have not necessarily been drawn to scale. For example, the dimensions of some of the elements in the figures may be expanded or reduced to help improve the understanding of the embodiments of the present invention. Moreover, while the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION OF EXEMPLARY EMBODIMENTS OF THE INVENTION

In the following description, for the purposes of explanation, numerous specific details are set forth in order to provide a thorough understanding of embodiments of the present invention. It will be apparent, however, to one skilled in the art that embodiments of the present invention may be practiced without some of these specific details.

Terminology

Brief definitions of terms, abbreviations, and phrases used throughout this application are given below.

The terms "connected" or "coupled" and related terms are used in an operational sense and are not necessarily limited to a direct physical connection or coupling. Thus, for example, two devices may be coupled directly, or via one or more intermediary media, devices, or structure. Based on the disclosure provided herein, one of ordinary skill in the art will appreciate a variety of ways in which connection or coupling exists in accordance with the aforementioned definition.

As used throughout the specification, the phrase "heat source" will be considered the location of the heat generated by the power electronics and/or the heat generated in the semiconductor or solid-state light source. Although variously described based on differences of technology and terminology well-known in the industry, the heat generated in the semiconductor or solid-state light source is typically considered to be localized in an LED die or in a slug, substrate or thermal sink with useful thermal transfer characteristics which is normally positioned opposite to the actual point of light emission of the LED or solid-state light source (also referred to herein as the "heat side" as opposed to the "light side"). Thus, as used throughout the specification, it is understood that while both light and heat are generated by the operation of the LED or solid-state light source as previously described, words and phrases such as "heat sink," "LED," "solid-state light source", "heat source," etc. will be used to describe the normal location of heat or means of heat extraction from an LED or solid-state light source. "Heat source" may also describe the power electronics or components, heat sink(s) associated with power electronics, and/or combinations of the power electronics and LED or solid-state lighting. In some embodiments, the power electronics may be close to the actual light source or located at some distance from the actual light source.

As used herein, the phrases "in some embodiments," "according to some embodiments," "in the embodiments shown," "in other embodiments," and the like generally mean the particular feature, structure, or characteristic following the phrase is included in at least one embodiment of the present invention, and may be included in more than one embodiment of the present invention. In addition, such phrases do not necessarily refer to the same embodiments or different embodiments.

"LED light(s) or LEDs" can refer to various types of LED or solid-state lights. These lights can vary widely in power consumed and/or efficiency, and include, but are not limited to, white or colored LED lights, infrared LED lights, and others. Some alternatives are mentioned previously.

If the specification states a component or feature "may", "can", "could", or "might" be included or have a characteristic, that particular component or feature is not required to be included or have the characteristic.

Lighting Theory of Operation

Typical conventional light sources used in occupied building spaces include incandescent, fluorescent and arc type fixtures. These fixtures are generally not affected by high temperature operation, at least relative to acceptable LED operating temperatures. Incandescent sources rely on a very high temperature filament in order to create light. Fluorescent lights have an optimum temperature and do not benefit from cooling beyond a certain point, below which point LEDs, in contrast, improve in longevity and reliability.

Incandescent and arc light sources both produce a significant amount of heat as infrared radiation. Arc type lamps also use a ballast for control of the lamp. These associated ballasts also produce heat as a by-product of operation.

In contrast to LED lamps, there is generally no benefit to increase power to the conventional lamps as a result of improved cooling, since modes of operation are quite different.

Incandescent lights use an electrical current to heat a filament to typically 2000 K to 3300 K (about 3100-5400° F.). Thus, they operate similarly to theoretical "black body radiators" with the result that most of the energy input into the lights is radiated as infrared light, with a small remainder effectively producing visible light. Typically, as much as 90% of the power consumed by an incandescent light bulb is emitted as heat, rather than as visible light. This results in a large amount of heat being introduced into the area lit by incandescent lights. At the same time, since waste heat is radiated away from the light source, these types of light sources, especially those used for general illumination, typically do not require extensive additional passive or active systems for removing waste heat.

Fluorescent lighting also typically (a) produces discrete spectral lines or bands of visible light and very with little infrared radiation, (b) creates additional heat from a ballast or the like; and (c) creates some heat at the source of illumination source. However, due to its unique shape, low light output per unit area of a typical fixture, and need to maintain a certain minimum temperature, it presents different considerations for heat management than envisioned herein.

Electrodeless lighting fixtures such as LIFI™ fixtures manufactured by LUXIM Corp., 1171 Borregas Avenue, Sunnyvale, Calif. 94089 (www.lifi.com) are a type of solid-state lighting. They are similar to arc type lighting, in that they use a capsule filled with gas and certain chemicals which is excited to a plasma state at several thousand degrees Kelvin to produce light. Unlike HID fixtures which use electrodes to produce an arc inside the capsule to create the plasma, they use solid-state driver electronics to create RF energy which is focused on the capsule to energize the gas and create the plasma effect. Since the capsule contents are very hot, a certain amount of radiant heat is emitted in the same location as the luminous energy (light). However since the fixtures use an electronic driver to create RF energy (which is physically proximate to the capsule but is ordinarily not visible to the room occupant) and may also use a separate DC driver/power source, this lighting source will be similar in thermal effect and cooling requirement to the LED assembly and/or driving electronics that may not be located in, or visible to, the living space. In accordance with some embodiments, other types or brands of electrodeless lamps could also be used.

LED Lighting—Heat Generation Theory

As is well known in the art, LEDs are composed basically of a semi-conductor material which emits light when electric current is applied. As a byproduct of operation, heat is also produced in the same location. However, unlike conventional lighting, LEDs generally produce light in discrete spectral lines within the visible spectrum; thus the heat produced by operation is not normally radiated (and thereby removed) from the LED assembly by means of infrared radiation. (It should be noted that some embodiments of the invention could use infrared LEDs (or LEDs emitting visible or IR light) for a particular application. Although IR radiation would therefore be present on the "light side", that radiation would not serve to remove the heat generated and present on the "heat side" of the LED assembly.) To prevent damage and to improve the efficiency of the LED, they are manufactured with various types of close-packaged heat sink arrangements to extract the heat by conduction to additional heat sinks or other means of heat extraction which are well known to those in the art.

The conductive path of heat rejection which results from these manufacturing methods is almost entirely in the non-emissive location (i.e. back side and sides but not the front side of the LED assembly). As a result, the functional source of heat from an LED is the "back side" of the assembly—i.e. the location away from the "front side" where the light is emitted. This division between a "light side" and a "heat side" makes it convenient to capture the waste heat in a way that is not possible with conventional lighting. Since the heat is concentrated in a location away from the "light side," the space which is illuminated by the LED can remain relatively unaffected by heat from the LED. The space on the "heat side" of the LED can be enclosed for efficient capture of heat. Enclosing the space can include a means or method of capturing, removing, and potentially repurposing the heat generated by LED operation. These means and methods can include the embodiments described herein.

LED Lighting Management

LEDs require and benefit from different heat management schemes than conventional lighting. In the range of normal ambient temperatures, LEDs typically benefit from reduced temperature resulting from either lower ambient temperatures or from various cooling schemes. In accordance with some embodiments, solid-state light sources may be able to be operated at higher wattage, and thus higher lumen output, due to the improved heat management from the fluid passing through the fixture. Cooling LEDs can allow them to operate at a higher current or power level, which can increase lumens per LED. This can allow the number of LEDs to be reduced. Because the cost of the LED assembly can be high compared with other fixtures on a lumen-for-lumen basis, reducing LED count can significantly reduce fixture cost. Cooling LEDs also can allow service life to remain relatively unchanged for an given increased current input/lumen output value, or to increase service life for a given current input/lumen output value, which can reduce maintenance and replacement costs. Unlike conventional lighting, there is no advantage to maintaining a temperature above ambient, and if adequate heat sinking is available, there could be considerable advantage to maintaining a significantly cooler temperature (for example, potentially down to "Arctic" temperatures on the order of −40° C.)

LED Lighting—Power Electronics

Heat can also be generated by power electronics that may be used to transform or condition current to energize and control the solid-state lighting. Power electronics may be mounted in close proximity to the solid-state lighting or may be located apart from the solid-state lighting. In either case, since the construction of the power electronics normally includes solid-state components such as diodes, transistors, and integrated circuits, the power electronic units require operating temperature limits similar to those needed for the solid-state lights. Thus although significantly less total waste heat may be generated by LED sources in comparison with other types of lighting, LED lights can contribute significantly more heat to the area in proximity to the fixture and/or driver. Other electronic components such as computers, processors, controllers, amplifiers, PA systems, etc. also typically contain sources of heat and which function similarly to LED power electronics.

Conditioned Space Considerations

Some embodiments of the present invention relate generally to heat management systems. More specifically, some embodiments of the present invention relate to heat rejection management in LED and other solid-state lighting fixtures and devices. For example, some embodiments use fluid transfer devices and various forms of fluid coolant management to reject heat from solid-state devices.

According to some embodiments, a system for cooling solid-state lighting fixtures can be used that includes a solid-state lighting source, an enclosure, and a fluid transfer conduit. The solid-state light source can include one or more light-emitting diode (LED) assemblies and a heat sink associated with power electronics and/or semiconductor material that is designed to control the solid-state light source. The solid-state light source can be mounted within the enclosure. In some embodiments, the enclosure includes a first side or portion that allows light from the solid-state light source to pass through to a target area. The enclosure can also have a second side or portion that thermally insulates the first side or portion of the enclosure (or is not considered to be effectively thermally coupled to the first side) from the heat sink that extends from a second side or portion of enclosure. A fluid transfer conduit can be connected to the second side or portion of the enclosure for passing a fluid across the heat sink to transport heat generated by the power electronics away from the heat sink of the solid-state light source.

In some embodiments of the present invention, multiple solid-state lighting devices can be connected through the fluid transfer conduit. Some enclosures can contain power electronics that may be mounted separately from the some or all of the solid-state light sources that they power. When the power electronics are mounted separately, some enclosures can have only solid-state light sources while some have both solid-state light sources and power electronics. In some embodiments, the power electronics may be located in an enclosure or assembly that is separate from any of the solid-state light sources.

Some embodiments of the present invention include a method for cooling solid-state lighting fixtures by determining the operating mode of a building HVAC system. Determining the operating mode of the building HVAC system can include determining if the whole system or parts thereof are delivering heated air, delivering cooled air, or operating in a ventilation only mode. Based on the operating mode of the building HVAC system, the heat generated by the heat sources associated with the lights can be rejected in a variety of manners.

In ventilation only mode, little or no heat is being added to or removed from the ventilated air by the HVAC system. Some embodiments of the present invention identify other building conditions that would suggest either transferring the heat to the occupied space, or transferring the heat elsewhere in accordance with embodiments of the present invention. For example, current building temperature, outside temperature, number of people using the building, and/or other factors may not be sufficient to justify the need to activate the HVAC heating sources. However, retaining heat within the building that has been generated by other sources may be beneficial (e.g., for economical operation). Similarly, current building temperature, outside temperature, number of people using the building, and/or other factors may not be sufficient to justify the need to operate the HVAC cooling sources. However, removing heat from the building envelope or from occupied spaces may be beneficial.

In accordance with some embodiments, if the HVAC unit is delivering heated air, the airflow through the HVAC ductwork can be routed from the HVAC ductwork across a set of power electronics designed to power a solid-state lighting source that is encased in an enclosure. According to some embodiments, the solid-state light source can be mounted so that a first side or portion of the enclosure allows light from the solid-state light source to pass through while a second side or portion of the enclosure thermally insulates the first side or portion of the enclosure from the set of power electronics that extends from a second side or portion of enclosure. By routing the airflow from the HVAC ductwork across the set of power electronics, a temperature of the airflow is increased by heat from the power electronics. In some embodiments, airflow with increased temperature can be routed back to the HVAC ductwork. For example, a fluid transfer conduit can interface with HVAC ductwork or directly with building interior or exterior areas through a radiator.

Temperature gain or loss must be considered based on operating parameters of the HVAC system and specification of the solid-state lighting systems. From these, calculations can be made to determine whether it is feasible or beneficial to use a particular source of air to cool the fixtures, and whether that air from the fixtures is then useful for heating applications. For instance, air in a HVAC system with a heat pump heat source may be on the order of 40° C. which could provide significant cooling for LEDs. If the air was heated by a fuel-type heat source, it might be significantly higher which might therefore be less desirable for cooling LED fixtures. These types of considerations and calculations will require knowledge of building system specifications, and are well known to those in the related industries.

Some embodiments include a method of cooling a lighting fixture and reducing the heat load contribution from the fixture for an interior space that is conditioned. Some embodiments pump air through the fixture to reduce the operating temperature of the light and exhaust the heated air outside the building when the air conditioning is operating. In some embodiments, the heated air can be optionally exhausted inside the building if the extra heat is desirable. Tubing or ducts, which could be small, can be routed to each fixture or interconnected between fixtures to create an exhaust network. The tubing may need to be insulated to prevent excessive heat loss from the tubing to the ambient air. For solid-state light sources, air ducts can be designed into the fixtures' heat sinks to maximize the heat transfer from the heat sink to the passing air.

Some embodiments of the present invention include multiple solid-state lighting sources that are each associated with a set of power electronics. The individual sets of power electronics are each encased in individual enclosures that include thermostats for monitoring the temperature of the enclosure. A determination can be individually made as to whether the temperature of each of the enclosures is above a threshold temperature. Based on the individual determinations, airflow from the HVAC ductwork and/or fluid conduits can be routed to the enclosures that are determined to be above the threshold temperature. In some embodiments, the enclosures are each associated with an independently controlled fan and wherein individually routing air from the HVAC ductwork and/or fluid conduits to the enclosures that are determined to be above the threshold temperature includes setting the fan to a desired speed.

In some embodiments, a system for cooling solid-state lighting fixtures can include a light source installed in a temperature-controlled area, ductwork, an apparatus for drawing heated fluid, and a controller. The light source can have an LED and a heat sink in thermal communication with a set of electronics designed to power the LED. The ductwork can be configured to encase the heat sink and to transport air into and out of the temperature-controlled area. The apparatus for drawing heated fluid (e.g., a fan or pump) can be designed to convectively remove heat from the heat sink and into the ductwork at a heat transfer rate. The controller monitors the temperature of the heat sink and adjusts the heat transfer rate based on the temperature of the heat sink. Examples of ways to adjust the heat transfer rate include, but are not limited to, varying the fan or pump speed or displacement, by cycling the fan or pump on and off, adjusting fluid flow rates, and others.

Some embodiments include a method of cooling a lighting fixture that is in a conditioned space (e.g., a building) or an unconditioned space (e.g., outside sports venue). In accordance with some embodiments, a system for cooling solid-state lighting fixtures can be provided by moving a fluid such as air, water, antifreeze solution, refrigerant (including phase-change refrigerants), or liquid coolant through the fixture to reduce the operating temperature of the lighting fixture and/or heat sources associated with the lighting fixture. In some embodiments, the fluid can be circulated through a heat exchanger that can exchange heat with a ground source, structures, cooling ponds, tanks, wells, reservoirs or other thermally receptive masses. The fluid circulation system may be part of an existing heating or cooling system, or may be installed in connection with installation of solid-state lighting fixtures.

One benefit of some embodiments of the present invention is that solid-state light sources may be able to be operated at higher wattage, and thus higher lumen output, due to the improved heat management of the fluid passing through the fixture. However, heat generated by the light sources is a problem. Although a fixture that is efficient and requires less energy to operate is beneficial, also beneficial to building designers, and ultimately the owners, is the reduction of the burden on the HVAC system created by some embodiments of the present invention.

Embodiments of the present invention may be provided as a computer program product that may include a machine-readable medium having stored thereon instructions that may be used to program a computer (or other electronic devices) to perform a process. The machine-readable medium may include, but is not limited to, floppy diskettes, optical disks, compact disc read-only memories (CD-ROMs), and magneto-optical disks, ROMs, random access memories (RAMs), erasable programmable read-only memories (EPROMs), electrically erasable programmable read-only memories (EEPROMs), magnetic or optical cards, flash memory, or other type of media/machine-readable medium suitable for storing electronic instructions. Moreover, embodiments of the present invention may also be downloaded as a computer program product, wherein the program may be transferred from a remote computer to a requesting computer by way of data embodied in a carrier wave or other propagation medium via a communication link (e.g., a modem or network connection).

While, for convenience, embodiments of the present invention are described with reference to LED heat management in buildings and LED heat management in open area lighting (e.g., light poles), embodiments of the present invention are equally applicable to various other lighting devices, lighting structures, building structures, and/or other types of enclosures. For example, some embodiments of the present invention can be used with boats, automobiles, planes, trains, tunnels, and other enclosed areas that need lighting. Others are possible, of course.

Likewise, while some embodiments refer to a building structure, building, space, or room, some embodiments of the present application are applicable to any enclosure or defined space that is generally referring to a structure that provides a distinction between two or more general areas. These general areas typically have differing needs or characteristics with regard to heating or cooling or the acceptability or desirability of adding and/or removing heat. For example, in some embodiments, the term building structure could be referring to a cabin, an enclosure, a capsule, a room, or any other structure that provides a distinction between two or more general areas. Others are possible.

Embodiments

Overview

FIG. 1 illustrates an example of an operating environment 100 in which some embodiments of the present invention may be utilized. Environment 100 shows a space or room 110 that is interior to a building that is temperature controlled. As shown in FIG. 1, the building has a heating ventilation and air conditioning (HVAC) unit and HVAC ductwork 120 installed throughout the building structure. (Alternatively, environment 100 could use a high velocity mini-duct system such as provided by Unico, Inc. (7401 Alabama Ave., St. Louis, Mo. 63111-9906 www.unicosystem.com) instead of conventional HVAC ductwork.) Lighting fixtures 130 provide light to room 110. In addition to light, most light fixtures produce some heat from the light source or the electrical system that provides power to the light fixture.

Specific Embodiments

Primary Embodiment

Figure 2A:
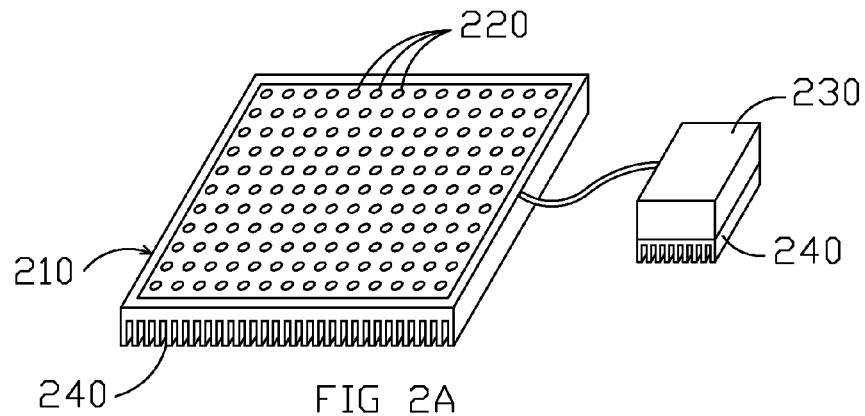
FIGS. 2A-2C illustrate various views of an example of a solid-state light source with power electronics, an enclosure, and fluid conduit that may be used in accordance with some embodiments of the present invention.
Figure 2B:
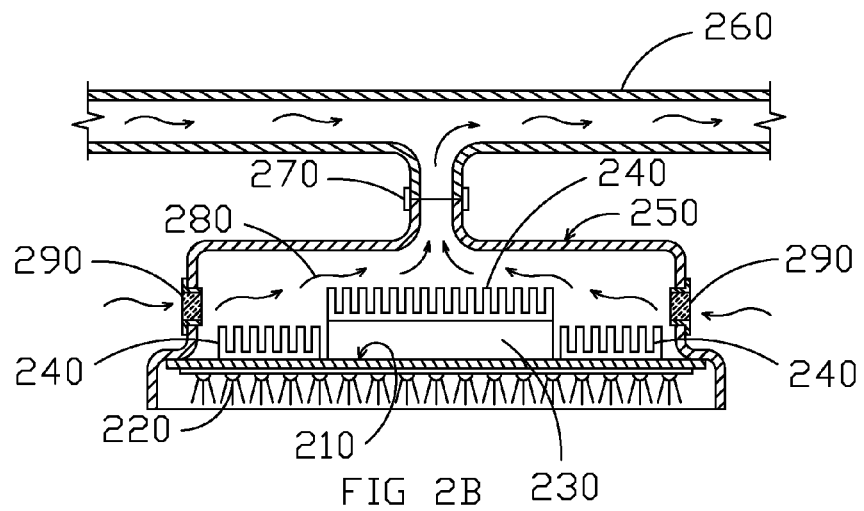
Figure 2C:
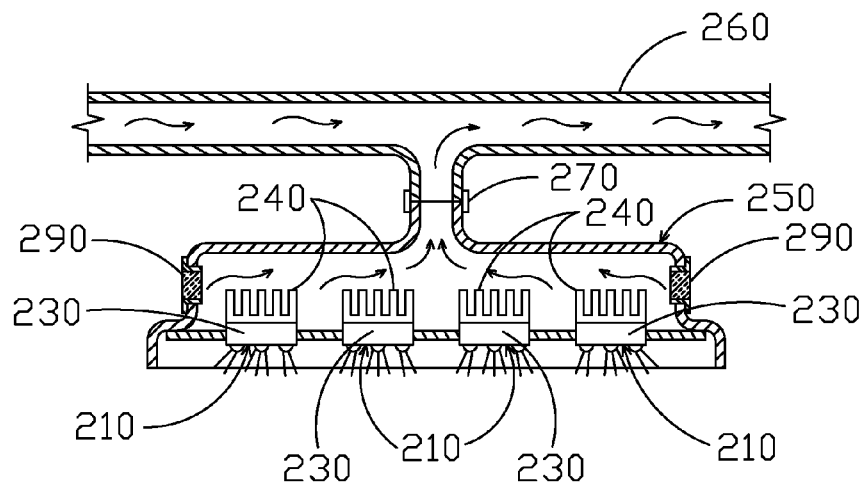

FIGS. 2A-2C illustrate various views of an example of a solid-state light source with power electronics, an enclosure, and a fluid conduit that may be used in accordance with some embodiments of the present invention. FIG. 2A is a perspective view of LED fixture 210 with an array of LED lights 220 that are powered by power electronics 230. Both LED lights 220 and power electronics 230 can use heat sinks 240 to dissipate heat. Power electronics 230 may be mounted directly on, in close proximity to, or remotely from fixture 210. LED lights 220 can be any type of LED or solid-state light.

Some embodiments of the present invention use solid-state lighting sources for interior applications. Since solid-state lighting sources generally have a "light side" which can be visible in the living space and which does not ordinarily need to be cooled, and since the "heat side" and the driving electronics do not need to be visible, heat is generally dissipated away from the LED substrate and/or driving electronics that may not be located in, or visible to, the living space. In accordance with some embodiments, heat dissipation can be accomplished with heat sinks 240 and thermal management methods developed for use with solid-state devices. For example, air ducts can be designed into the fixtures' heat sinks to maximize the heat transfer from the heat sink to the passing air.

In addition to heat sinks, some embodiments of the present invention pump or allow convective flow of fluid (e.g., air or coolant) through the fixture and across the heat sinks to reduce the operating temperature of the light. FIG. 2B is a cross-sectional view of a fixture or enclosure 250 attached to fluid conduit 260 in accordance with some embodiments of the present invention. LED fixture 210 includes one or more arrays of LED lights 220 that are powered by power electronics 230 and can be mounted within enclosure 250. Various types of conduit can be used to conduct or transmit fluid. Examples of types of fluid conduit 260 that can be used in accordance with some embodiments include, but are not limited to, PVC, ABS, CPVC, PE, PB, PEX tubing (rigid or flexible); fiberglass, metal, or plastic ductwork, or other types of structures that can effectively provide a passageway for vapor or liquid.

In some embodiments, mounting fixture or enclosure 250 is configured to encase the heat sink 240 within what will be called a "heat chamber" (e.g. see FIGS. 2B and 2C). The heat chamber can be designed to isolate the heat generated by the power electronics and/or semiconductor material from a temperature-controlled area (e.g., room 110 in FIG. 1). In some embodiments, the heat chamber can include an opening that allows the heat chamber to be connected to the fluid transfer conduit 260 to allow for the transfer of heat away from the heat chamber. In some embodiments, vent/filter combination 290 allows ambient air to be drawn into the fixture and exhausted through fluid conduit 260. In some embodiments, the fixture can have separate connections to 'supply' fluid conduit 360 and 'exhaust' fluid conduit 365 as illustrated in FIG. 3A and FIG. 4.

As illustrated in the cross section of FIG. 2B, mounting fixture or enclosure 250 can include interface 270 that is designed to connect enclosure 250 with fluid conduit 260. Various mounting methods can be used at interface 270 to attach mounting fixture 250 with fluid conduit 260. Examples of ways to attach fixture 250 with fluid conduit 260 that can be used in accordance with some embodiments include, but are not limited to, clamps, screws, bolts, snap fits, pressure fits, welds, epoxies, solvents, adhesives and others.

The heated air 280 created by the semiconductor material and/or associated driving electronics can be exhausted outside the building using fluid conduit 260 when the air-conditioning is operating and optionally exhausted inside the building if the extra heat is desired. In accordance with some embodiments, fluid conduit 260 can include small tubing that is routed to each fixture or interconnected between fixtures to create an exhaust network. The tubing may or may not be insulated to prevent excessive heat loss from the tubing to the ambient air.

FIG. 2C is a cross-sectional view of enclosure 250 attached through interface 270 to fluid conduit 260 in accordance with some embodiments of the present invention. As shown in FIG. 2C, LED fixture 210 can include multiple LED arrays with separate semiconductor and associated driving electronics 230. The semiconductor and/or associated driving electronics 230 can be mounted inside the enclosure within a heat chamber that is separated from the LED light side of the enclosure. As a result, heat from the semiconductor and/or associated driving electronics 230 is captured and contained in the heat chamber until exhausted through fluid conduit 260. The heat chamber may also be constructed to be thermally insulated from the LED light side or otherwise insulated or isolated. Thermal insulation techniques can include simply using interstitial material with a relatively low thermal transfer rate, such as using various plastics or fibrous materials instead of metals such as steel, aluminum, zinc, copper, etc. In some embodiments, more aggressive techniques can be used that include, but are not limited to, using more insulative materials. Examples of insulative materials include, but are not limited to, extruded or expanded polystyrene foams, polyurethane foam, fiberglass fibers, ceramics, and the like.

First Additional Embodiment

FIGS. 3A-3B illustrate examples of reflective lighting enclosures that may be used in some embodiments of the present invention. FIG. 3A is a cross-sectional view of a first side of lighting enclosure 310 while FIG. 3B is a cross-sectional view of a second side of lighting enclosure 310. As shown in FIGS. 3A-3B, lighting enclosure 310 includes an array of LEDs 320 pointed toward a reflective surface 330 on the inside of lighting enclosure 310. The light 370 (FIG. 3B) emitted from LEDs 320 is reflected from reflective surface 330 toward the target area through transparent plates or covers 380. Examples of reflective materials that can be used in some embodiments of the present invention include, but are not limited to, various surfaces of metal and/or plastic that can be embossed, patterned, and/or otherwise configured for light spread or diffusion. In some embodiments, surfaces of the reflective material can be matte, burnished, semi-specular, specular, etc. Other examples include a frame or surfaces coated or layered with reflective material including but not limited to very high reflectivity material (e.g. MIRO®).

In the embodiments shown in FIGS. 3A-3B, the LED semiconductor material and/or associated driving electronics are associated with heat sink 340 in a thermally separate section or enclosure/chamber 350 below enclosure 310. While shown in the center in FIG. 3B, section 350 can be located along any portion of the enclosure. However, when section 350 is located in different positions, reflective surface 330 and/or LEDs 320 may be angled differently so that light 370 is reflected through transparent plates/covers 380 that may also be in different locations.

Section 350 can be connected to one or more fluid conduits 360 (FIG. 3A) that allow air or other coolant to be directed through the fixture to reduce the operating temperature of the LED semiconductor material and/or associated driving electronics along with heat sink 340. Fluid conduit 360 allows, e.g., the heated air to be exhausted outside the building when the air-conditioning is operating and optionally exhausted inside one or more portions of the building if the extra heat is desired. As will be described in more detail below, the heat generated by the lighting fixtures may be captured and used to reduce the energy usage of the building. For example, the heat can be used to charge batteries, heat water, stored in electrical storage devices, power LED lights, and in other ways. Other heat transfer or exchange methods and mediums are possible.

Second Additional Embodiment

FIG. 4 illustrates an individually controlled enclosure 400 that may be used in accordance with some embodiments of the present invention. Individually controlled lighting enclosure 400 can include an array of LEDs 420 pointed toward a target area outside of lighting housing 410. On the top or side of lighting housing 410 may be a thermally separated housing 430 that encloses the heat sinks, LED substrates/heat sinks, and/or associated driving electronics of the array of LEDs 420. Individually controlled fan or blower 440 can be used to move air across the heat sinks, LED substrates and/or associated driving electronics of the array of LEDs 420. In some embodiments, the individually controlled fan or blower 440 can run 'open loop' (e.g., on a timed interval, whenever the LEDs are turned on, etc) or 'closed loop' using thermostat 450 within housing 430 to regulate the temperature in housing 430 within a desired range. Those of skill in the art can select specifications for fans, blowers, or other related components such as needed for the application used.

In accordance with some embodiments, thermally separated housing 430 can be connected to one or more fluid conduits 460. Airflow 470 is drawn in through fluid conduit 460 by the individually controlled fan or blower 440, across the LED substrates and/or associated driving electronics, and out a second fluid conduit 480.

Third Additional Embodiment

Figure 5A:
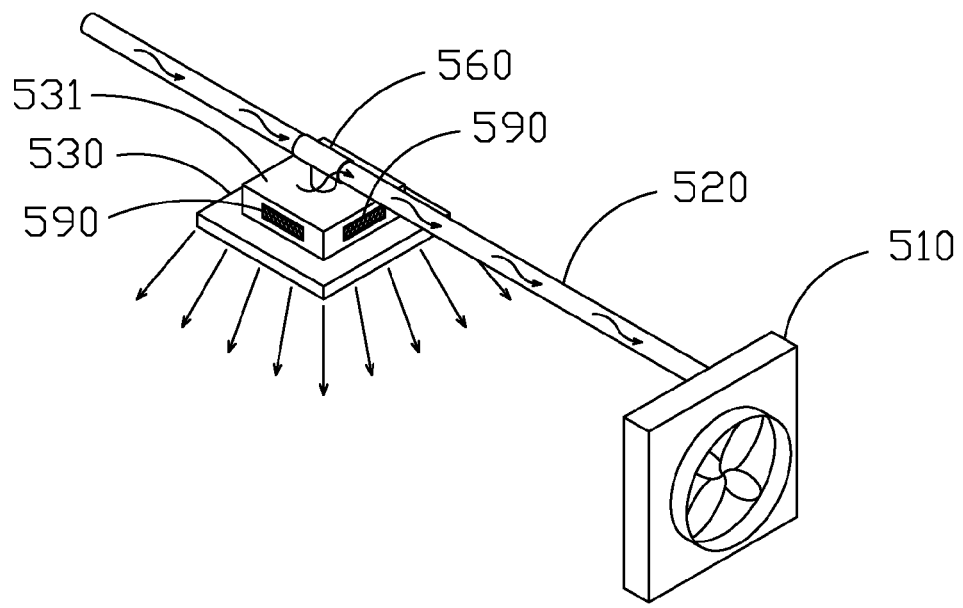
FIGS. 5A-5E illustrate examples of enclosures and fluid conduits that may be used in accordance with some embodiments of the present invention.
Figure 5B:
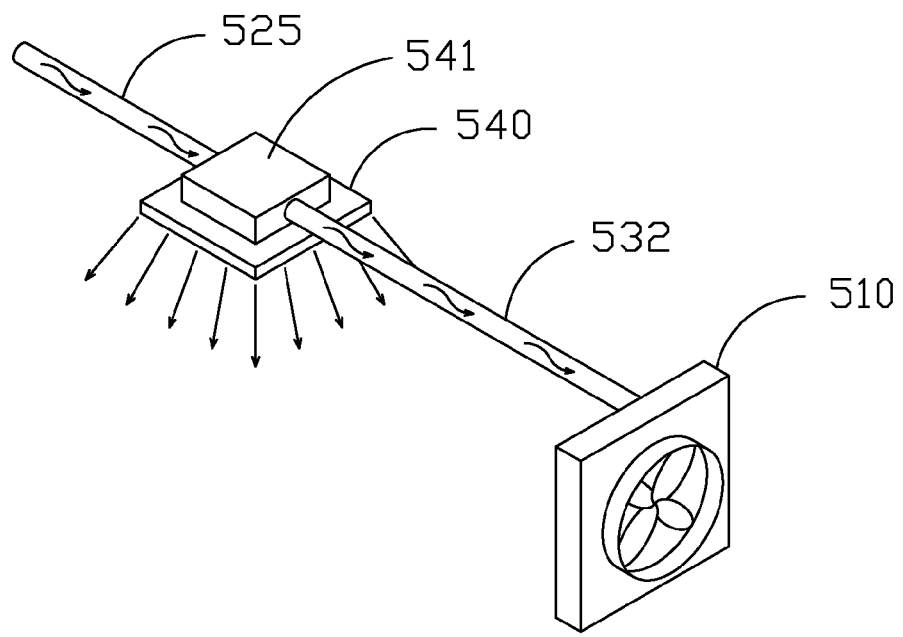

FIGS. 5A-5D illustrate examples of enclosures and fluid conduits that may be used in accordance with some embodiments of the present invention. As illustrated in FIGS. 5A and 5B, some embodiments of the present invention may use a fan or blower 510 to pull air through fluid conduit 520. The fan or blower 510 can pull air from outside the building structure and/or temperature-controlled air from inside the building structure. In some embodiments, the fan 510 can be located externally to a building structure or on an outside wall. The heated air created by pulling the air over the LED substrates, or power electronics associated with one or more arrays of LEDs can be exhausted to the outside of the building structure through a vent. While the embodiments shown in FIGS. 5A and 5B show a fan or blower 510, other embodiments can use a fluid pump or other device to move a liquid (e.g., cold water) or gas through the fluid conduit.

According to some embodiments of the present invention, fluid conduits 520 can interface with lighting enclosure 530 and 540 in a variety of ways. For example, as illustrated in FIG. 5A, fluid conduit 520 interface(s) with lighting enclosure 530 through an opening in a thermally separated section 531 that houses the LED substrates, and/or power electronics of the LED array. The fluid flow through fluid conduit 520 creates a low pressure at fitting 560. In some embodiments, fitting 560 can be a venturi-type fitting such as, for example, the LASCO Fittings Venturi Tee available from Lasco Fittings Inc. of Brownsville Tenn. As a result, the ambient air is drawn through vents 590, into the thermally separated section where it cools the heat sink, and is exhausted through fluid conduit 520.

FIG. 5B illustrates a lighting enclosure 540 that may be used in some embodiments of the present invention. As illustrated fluid conduit 525 interface(s) with lighting enclosure 540 through an opening in a thermally separated section 541 that houses the LED substrates, and/or power electronics of the LED array. This allows fluid to flow into and out of a heat chamber or thermally separated enclosure (e.g., 565 in FIG. 5C) that is within a section of lighting enclosure 540 or 541. Fluid exits section 541 through conduit 532. Alternatively, air can be drawn over the heat side(s)/heat sink(s) without the sealed/insulated chamber.

Figure 5C:
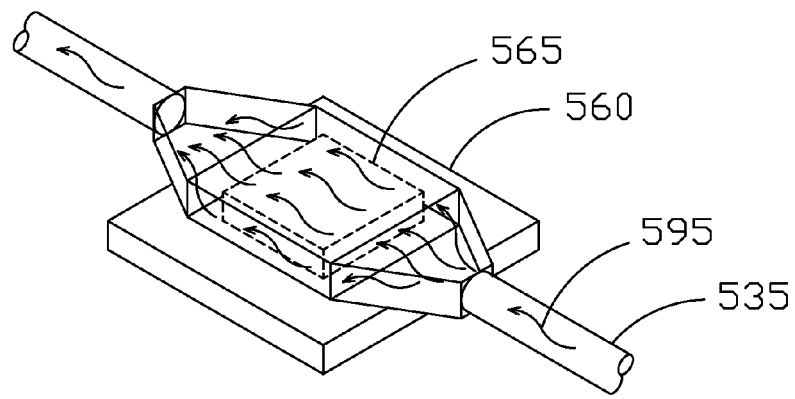
Figure 5D:
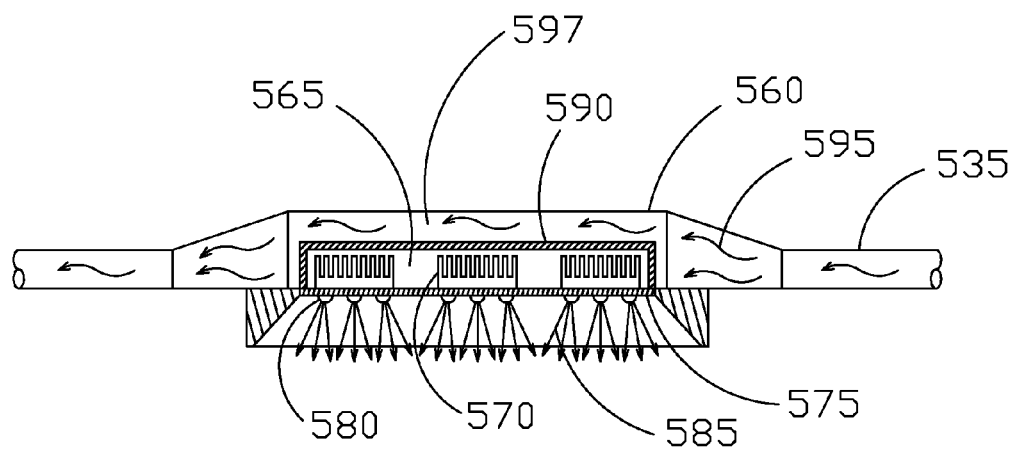

FIGS. 5C and 5D show a perspective and side view, respectively, of an example of a lighting enclosure 560 that may be used in some embodiments of the present invention. As shown in FIGS. 5C and 5D, lighting enclosure 560 includes a sealed portion 565 that creates a heat chamber where the LED substrates, and/or power electronics and associated heat sinks 570 may be housed. A gap or space 597 can exist between the walls 590 of sealed portion 565 and the walls of enclosure 560 so that a fluid is able to flow in the gap or space.

Figure 5E:
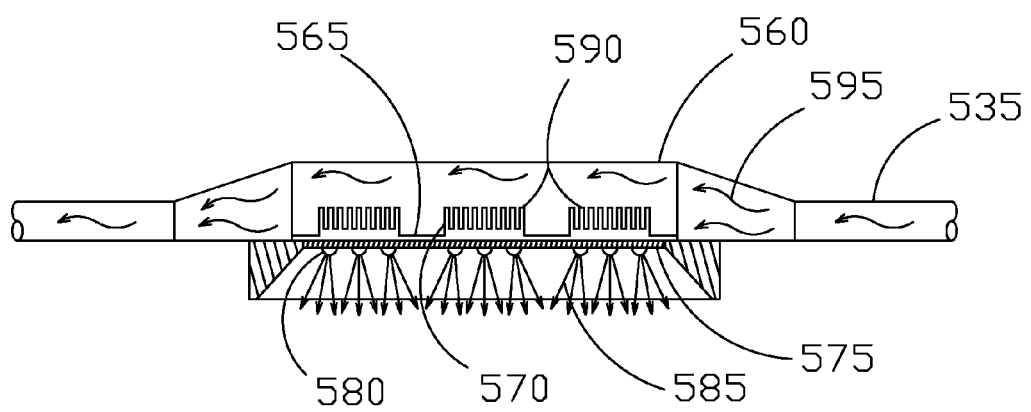

A first side 575 of the sealed portion 565 between the LED substrates, and/or power electronics and the array of LEDs 580 that emit light 585 may be thermally insulated, e.g. from the room or space on the "light side". The other sides 590 of the sealed portion 565 may be thermally conductive to allow for the transfer of heat from heat sinks 570, if present, and the LED substrates, and/or power electronics. In accordance with some embodiments, a fluid 595 can be transferred through fluid conduit 535 by a fan or blower 510 (see, e.g., FIGS. 5A and 5B) or a fluid pump (not shown). In some embodiments, the sidewalls of enclosure 560 may also be thermally insulated, and the fluid is able to flow in the gap between the walls 590 and walls of enclosure 560 extracting heat being dissipated by heat sinks 570 and/or LEDs and/or power electronics. In accordance with some embodiments, FIG. 5E illustrates sealed portion 565 formed by connecting and sealing heat sinks 570 and/or the surface of the LED assembly to form sides 590.

Fourth Additional Embodiment

Figure 6:
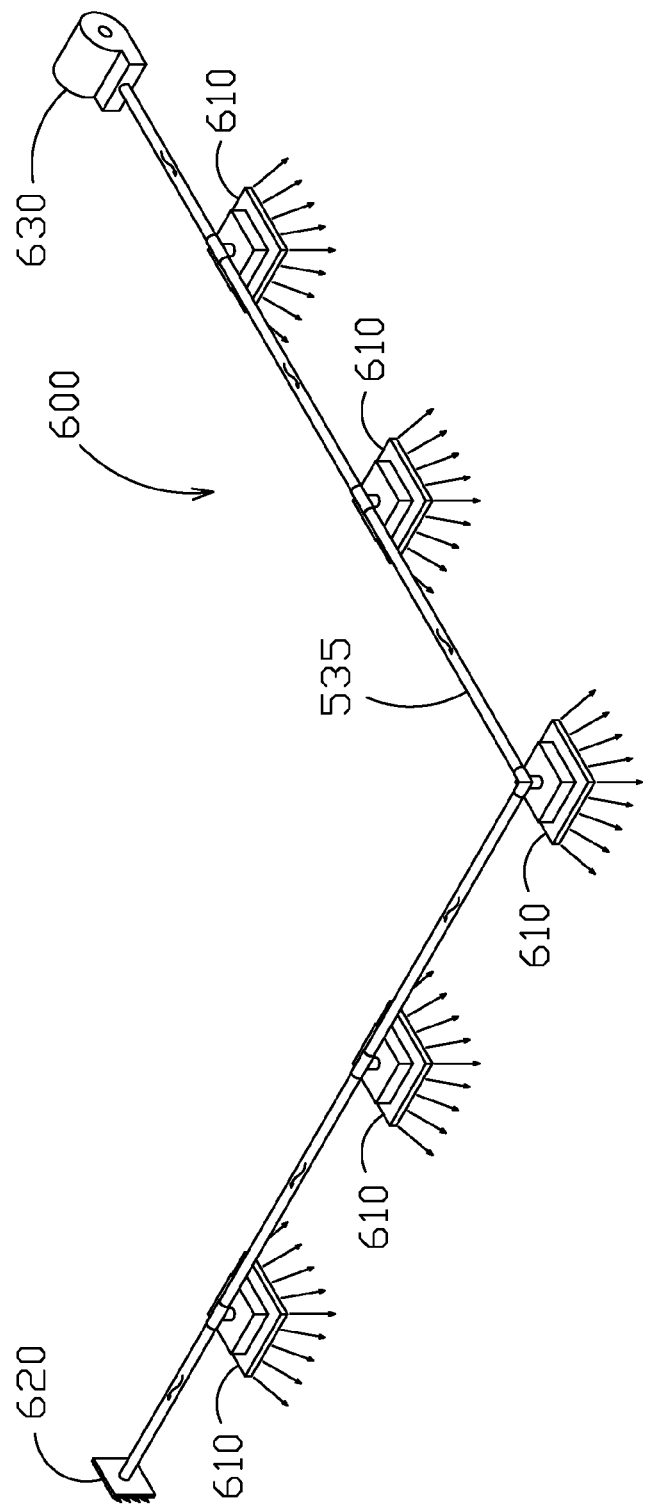
FIG. 6 illustrates a fluid conduit connecting multiple lighting sources and enclosures that may be used in accordance with some embodiments of the present invention.

FIG. 6 illustrates how fluid conduit 535 may connect multiple lighting enclosures 610 in system 600. If the fluid is ambient air, for example, then the fluid may be externally exhausted through vent 620. In contrast to the embodiments shown in FIGS. 5A and 5B, FIG. 6 illustrates a blower 630 that is pushing air past the lighting fixtures 610.

Fifth Additional Embodiment

In accordance with some embodiments, the utility savings from exhausting the fixture heat from the building during cooling cycles and redirecting the heat inside during heating cycles will vary with the weather conditions of the region. For example, warm climate regions with extended cooling cycles may have greater savings than cold climates with predominantly (at least in certain seasons) extended heating cycles. Some embodiments of the present invention provide for the heat produced by various components associated with the LEDs to be captured and/or converted to other types of energy. For example, in some embodiments, the heat may be used to heat the air used by the HVAC system, to heat water, to charge batteries or capacitors, and other exchanges of energy that may lower utility demand.

Figure 7A:
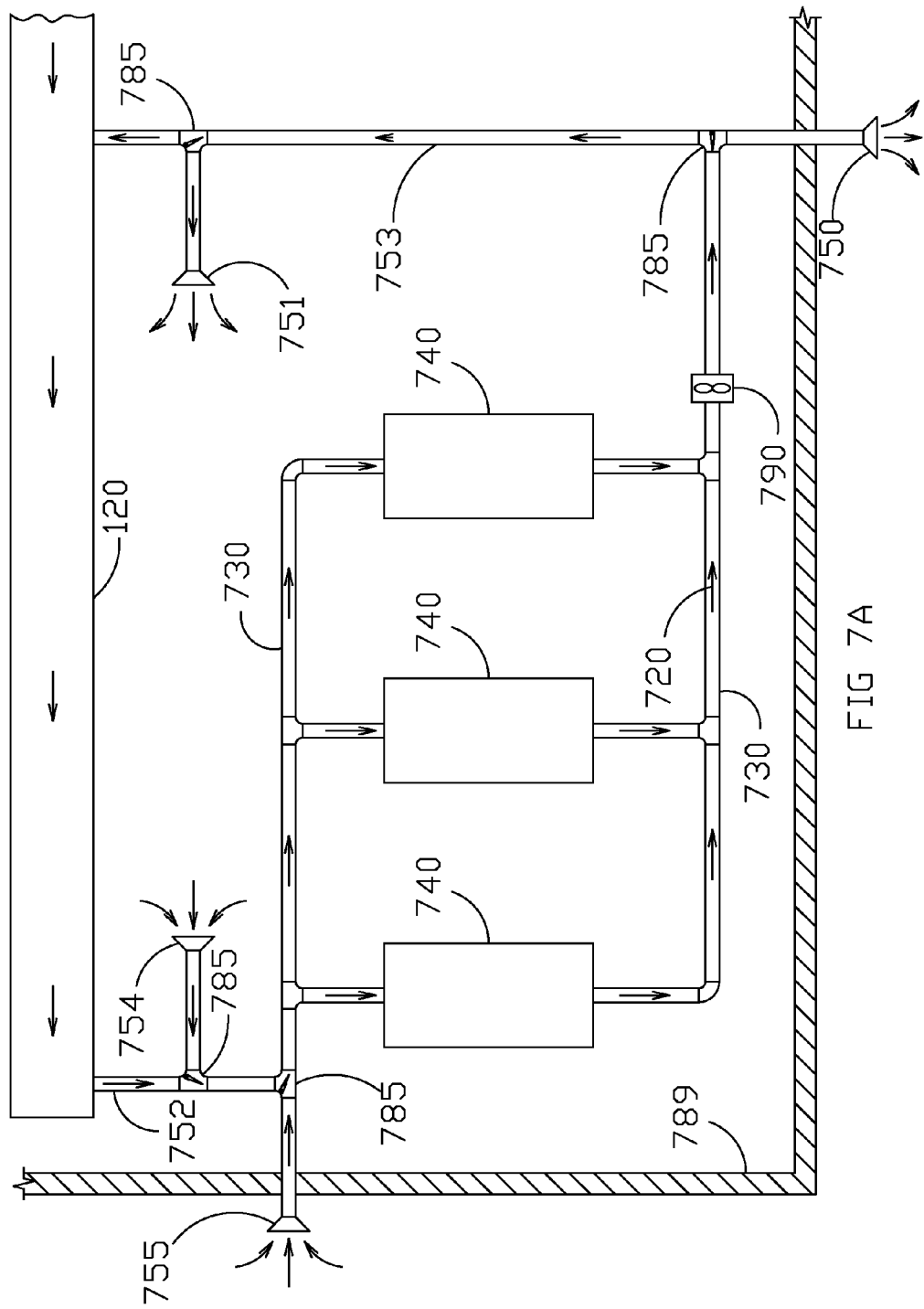

FIG. 7A illustrates an example of an operating environment in which some embodiments of the present invention may be utilized. As illustrated in FIG. 7A, some embodiments of the present invention can use a fan or blower 790 to create airflow 720 from inlet 755, through fluid conduit 730 that connects one or more lighting enclosures 740. Fluid conduits can be exhausted to HVAC exhaust ducts 120 through fluid conduit 753, into occupied space 789 through vent 751, and/ or to the outside through vent 750 depending on whether the HVAC is cooling or heating the building. Exhaust locations could optionally be only one or some of these locations, or the system could include and allow use of any or all of those exhaust choices according to operating conditions.

In some embodiments, air can optionally be drawn from HVAC duct 120 through fluid conduit 752 instead of, or in addition to, inlet 755, and/or from interior space inlet 754. The system can include and allow use of any or all of available inlet choices according to operating conditions. Examples of operating conditions include, but are not limited to, HVAC mode (e.g., set to heat, cool, fan only, off, etc.), temperatures of one or more building rooms or enclosures, temperature external to the building, desired temperature in building rooms or enclosures, thermostat settings, manual override settings, and others.

If needed, a directional valve 785 such as are commercially available and known in the art, FIG. 7A-7C can be used to control airflow. FIG. 7C shows directional valve 785 directly airflow by being positioned in two different positions. In some embodiments, the valve may be positioned in between the two positions shown in FIG. 7C allowing fluid to flow at a variety of different rates in two directions. An actuator (manual or automatic controlled) 795, FIG. 7C changes its states. Examples of types of flow control devices can be seen at U.S. Pat. No. 7,331,383 and U.S. Patent Application Publication Nos. US 2009/0007978, and US 2009/0100702, each of which is incorporated by reference herein.

The exhaust locations and/or air draw locations can be selected using one or more of a variety of methods according to various embodiments of the present invention. Some embodiments allow these locations to be adjusted manually and/or automatically. For example, HVAC system controls or thermostat type controls can be used to monitor the temperature of various sections of the building. This information can then be used to adjust the exhaust and/or air draw locations in order to adjust the temperatures of the various building sections.

Some embodiments of the present invention as shown in FIG. 7B include a device 760 to convert captured heat into electrical energy that can be stored in one or more batteries 770 and/or to heat water that can be stored in water tank 780. Device 760 can be e.g. a thermopile or peltier effect device such as are known and commercially available. The thermoelectric effect is the direct conversion of temperature differences to electric voltage and vice versa. A thermoelectric device creates a voltage when there is a different temperature on each side. Conversely when a voltage is applied to it, it creates a temperature difference (known as the Peltier effect). At atomic scale (specifically, charge carriers), an applied temperature gradient causes charged carriers in the material, whether they are electrons or electron holes, to diffuse from the hot side to the cold side, similar to a classical gas that expands when heated; hence, the thermally-induced current.

One benefit of this type of system is the ability to reduce the utility demand charges for the facility. Since demand charges are based on the highest, i.e., peak, usage over a defined time interval, a reduction in the peak usage should result in cost savings on the utility expense. By exhausting the heat from the fixtures out of the building, the cooling needs of the facility are reduced, thus reducing the energy consumption. In addition to simply exhausting the heat out of the building, some embodiments of the present invention can be used to reduce the demand charges by charging electrical storage devices (e.g., batteries 770) and then using power from storage devices during peak demand periods. This method reduces the peak energy consumption of the fixtures by spreading out lower energy consumption to the storage devices over long periods.

In some embodiments, some or all of the energy used by the fixtures can be pulled from the storage devices and not directly from the utility grid. Solid-state light sources are good candidates for operating off a storage device since solid-state lights can operate directly on the direct current (DC) storage power. However, other embodiments can provide power to other devices within the building that operate on DC storage power. By using the storage devices to power devices that operate directly on DC, the need to convert the stored energy to alternating current (AC) is eliminated, which improves the efficiency and reduces the system cost. As a result, some embodiments can provide an estimated potential savings of ten to fifteen percent per year. While less efficient, some or all of the stored energy can be converted to AC current.

Additional Embodiments

Additional Thermal Systems

Some embodiments of the present invention provide for a heat exchange between solid-state lighting fixtures and building cooling/heating systems that use circulating fluid, such as conventional or ground source (geothermal) heat pumps, hot water heating systems, or chilled water/coolant systems. Accordingly, LED lighting cooling circuits may be plumbed with heat exchangers in close proximity to the lighting heat source in buildings with coolant or heat sources that circulate in, for example, ceiling cavities, crawl spaces, and the like.

In some embodiments, a system for cooling solid-state lighting fixtures can include heat exchangers that are not in close proximity to the lighting heat source in buildings with coolant or heat sources that are more centralized, or distant, but which may still be close enough to provide benefits. During warm weather when removing excess heat from the building is desirable, this type of structure can prevent heat from LED or other heat sources from reaching occupied space. During cold weather, heat from the LED or other sources can be captured and directed to occupied space.

Some embodiments of the present invention provide for an exchange of thermal energy between LED lighting fixtures and building cooling/heating systems other than HVAC systems. For example, some embodiments of the present invention can interface with building cooling/heating systems that use circulating fluid. Examples of building heating/cooling systems that use circulating fluid include, but are not limited to, geothermal heat pumps, ground-coupled heat exchangers, and others known to those of ordinary skill in the art. Heat transfer principles based on thermal conductivity of materials, temperature differentials between fluids, thermal transfer capacity based on specific heat, viscosity, etc. of various fluids, as well as thermal receptivity of ground or ground water heat sinks, are well-known to those having ordinary skill in the art. These individuals will be able to consider and calculate appropriate heat transfer models given building conditions, operating characteristics and temperature limits of solid-state lighting, flow and pressure parameters of heating or cooling systems, comparisons of radiant and convective heat transfer mechanisms, etc.

Sixth Additional Embodiment

Figure 8A:
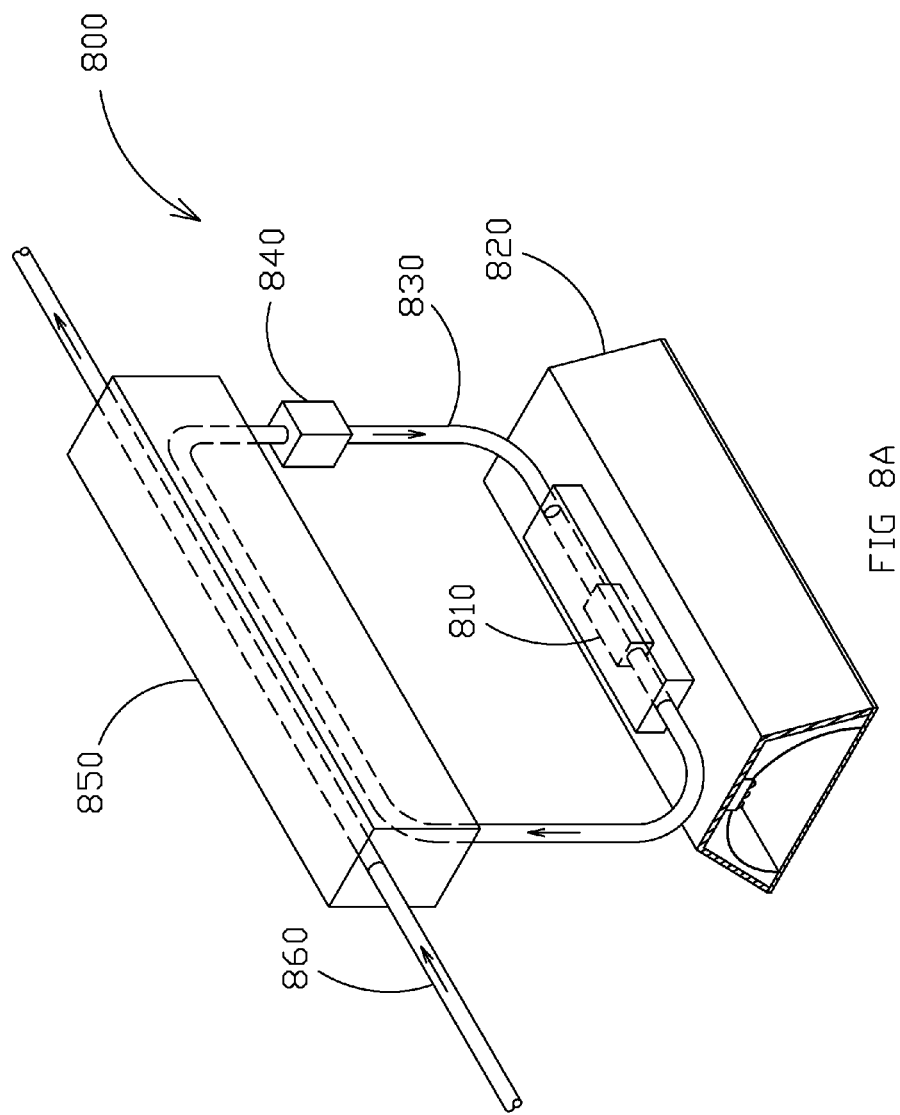

FIGS. 8A-8G illustrate an example of a system with a heat exchange between LED lighting fixtures and building cooling/heating systems that use circulating fluid that may be used in some embodiments of the present invention. FIG. 8A shows a cooling system 800 that uses circulating fluid to cool a heat source 810 (e.g. solid-state light source(s) and/or power electronics) in fixture 820. The coolant in tubing 830 can be circulated by pump or fan 840 and is cooled by a heat exchange system 850 with building heating/cooling system circulating fluid in tubing 860. Various types of heat exchange methods know to those of ordinary skill in the art could be used depending on many considerations. For instance, the heat sink and/or electronics components can be sealed against fluid leakage such that fluid could be directly circulated past the heat sink fins or across the surface of the electronics enclosures. Alternatively, the heat sink can be thermally connected with a plurality of fins in a tube and fin type cooler such as used in vehicle radiators or heater cores. Heat sinks can be tubular (hollow) for fluid flow with interior fins or surface conditions to encourage efficient transfer of heat.

Figure 8B:
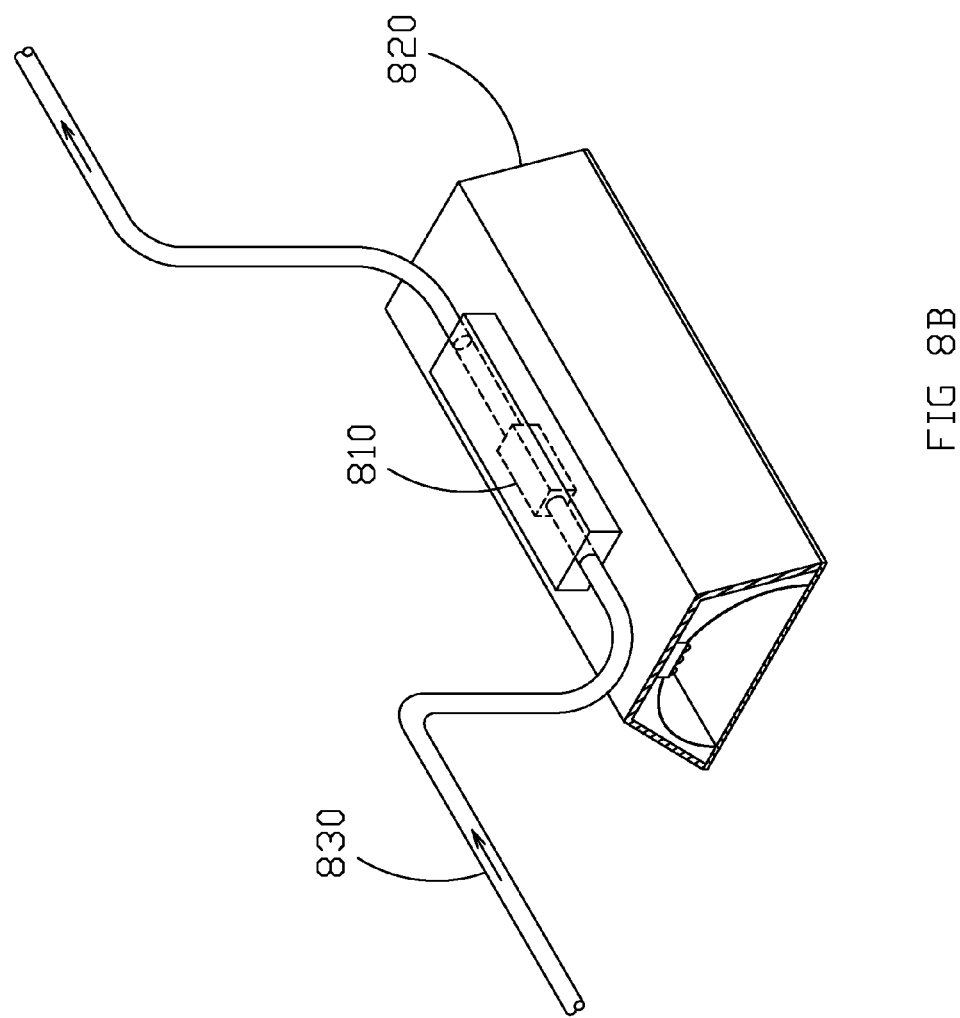

FIG. 8B shows a cooling system that can be used with building heating/cooling system circulating fluid in tubing 830 in accordance with some embodiments of the present invention. Fluid in tubing 830 can be used to directly cool heat source 810 in fixture 820 by flowing on or around the heat sink, thereby removing the heat.

FIG. 8C shows a cooling system that uses a remote building chiller system in accordance with some embodiments of the present invention. As shown in FIG. 8C, the cooling system uses circulating fluid to cool heat source 810 in fixture 820. The coolant in tubing 830 can be circulated by pump or fan 840 and can be cooled by remote heat exchanger 870 that may lie on the other side of a building wall, floor, ceiling, or other divider 875. Remote heat exchanger 870 can be cooled, for example, by building chiller system coolant in tubing 860 from chiller unit 895 as known and commercially available.

Figure 8D:
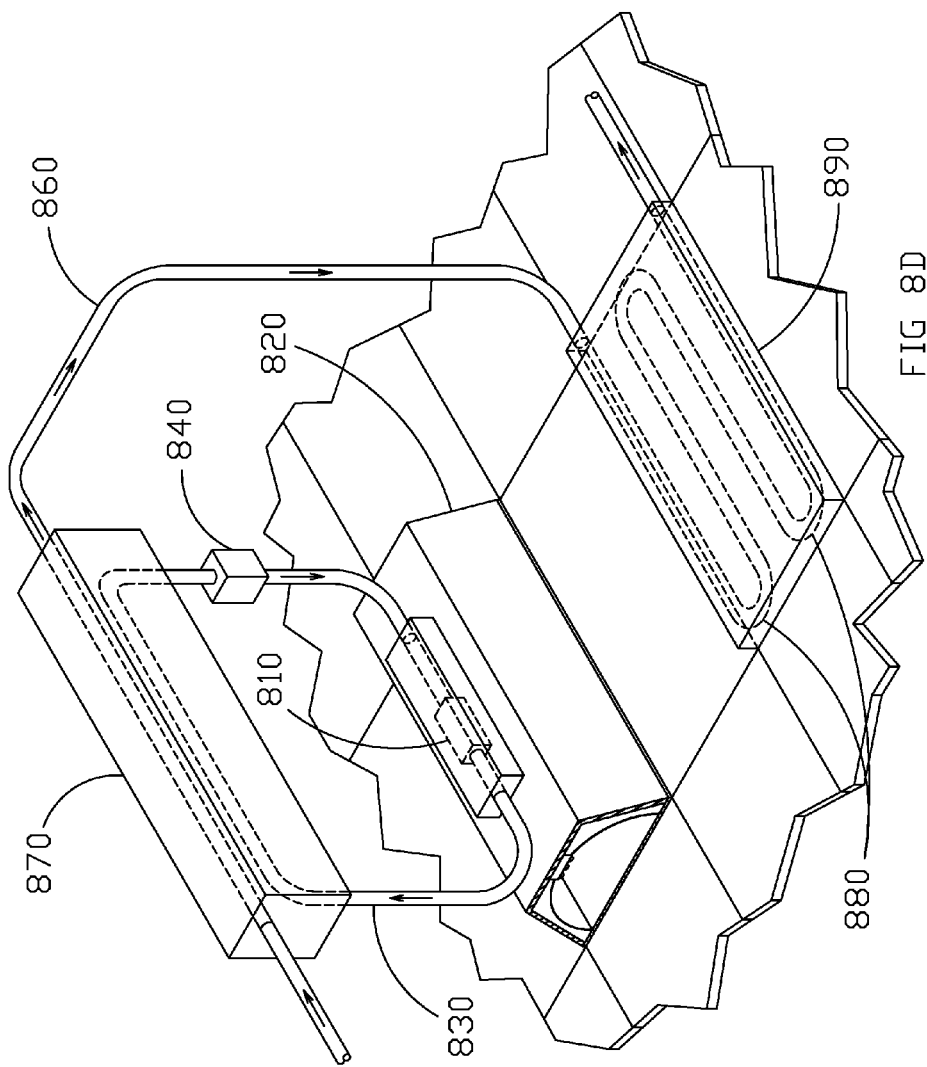

FIG. 8D shows a system for cooling light fixtures that use a geothermal or other fluid-filled radiant heating system to supply heat to building occupants that may be used in accordance with various embodiments of the present invention. The coolant in tubing 830 can be circulated by pump or fan 840. The coolant can then be cooled by a heat exchange system 870 with building system heat transfer fluid in tubing 860. Tubing 860 supplies warmed fluid to loops 880 in ceiling radiant panel 890. In other embodiments, the radiant heating system could be in the floor, walls, or any other available surface. Some embodiments of the present invention can be configured to exchange with building heating/cooling fluid either prior to or after the building fluid receives or releases heat from other heat exchange systems. This allows the building design to be optimized for climatic conditions and for varying operating conditions.

Figure 8E:
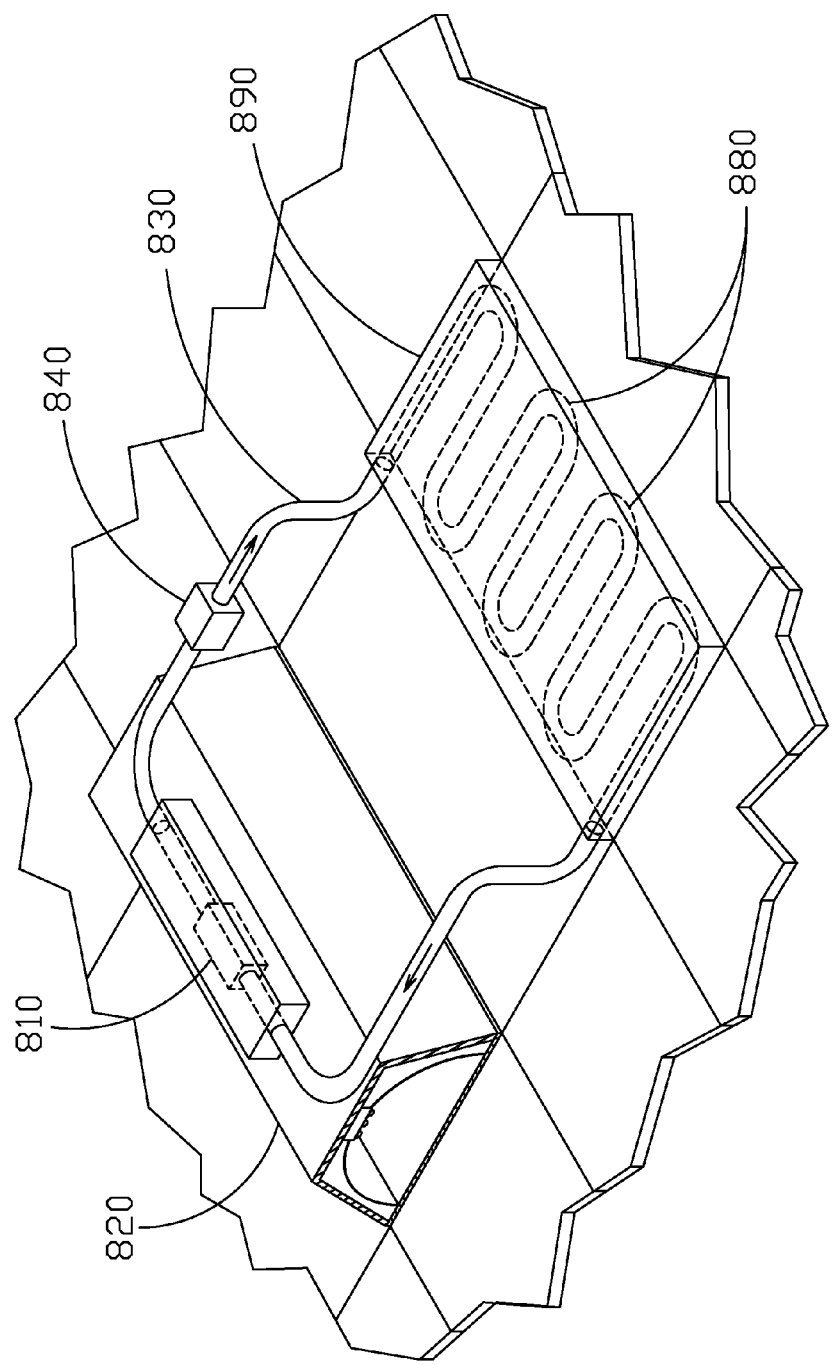

FIG. 8E shows a system for cooling light fixtures that supplies heat directly to a radiant heating system that may be used in accordance with various embodiments of the present invention. The fluid in tubing 830 can be circulated by pump or fan 840. The circulation supplies warmed fluid to loops 880 in ceiling radiant panel 890 that causes heat to be radiated to the room below. In other embodiments, the radiant heating system could be in the floor, walls, or any other available surface.

FIG. 8F shows a system similar to FIG. 8D in which geothermal fluid or other building system fluid is used to cool heat source 810 in fixture 820. As illustrated in FIG. 8F, the fluid then circulates directly to loops 880 in ceiling radiant panel 890.

FIG. 8G shows a system similar to FIG. 8E in which fluid or other building system fluid is used to cool heat source 810 in fixture 820, which fluid then circulates directly to heating coil 895 which is enclosed in HVAC duct 120.

Seventh Additional Embodiment

Figure 9:
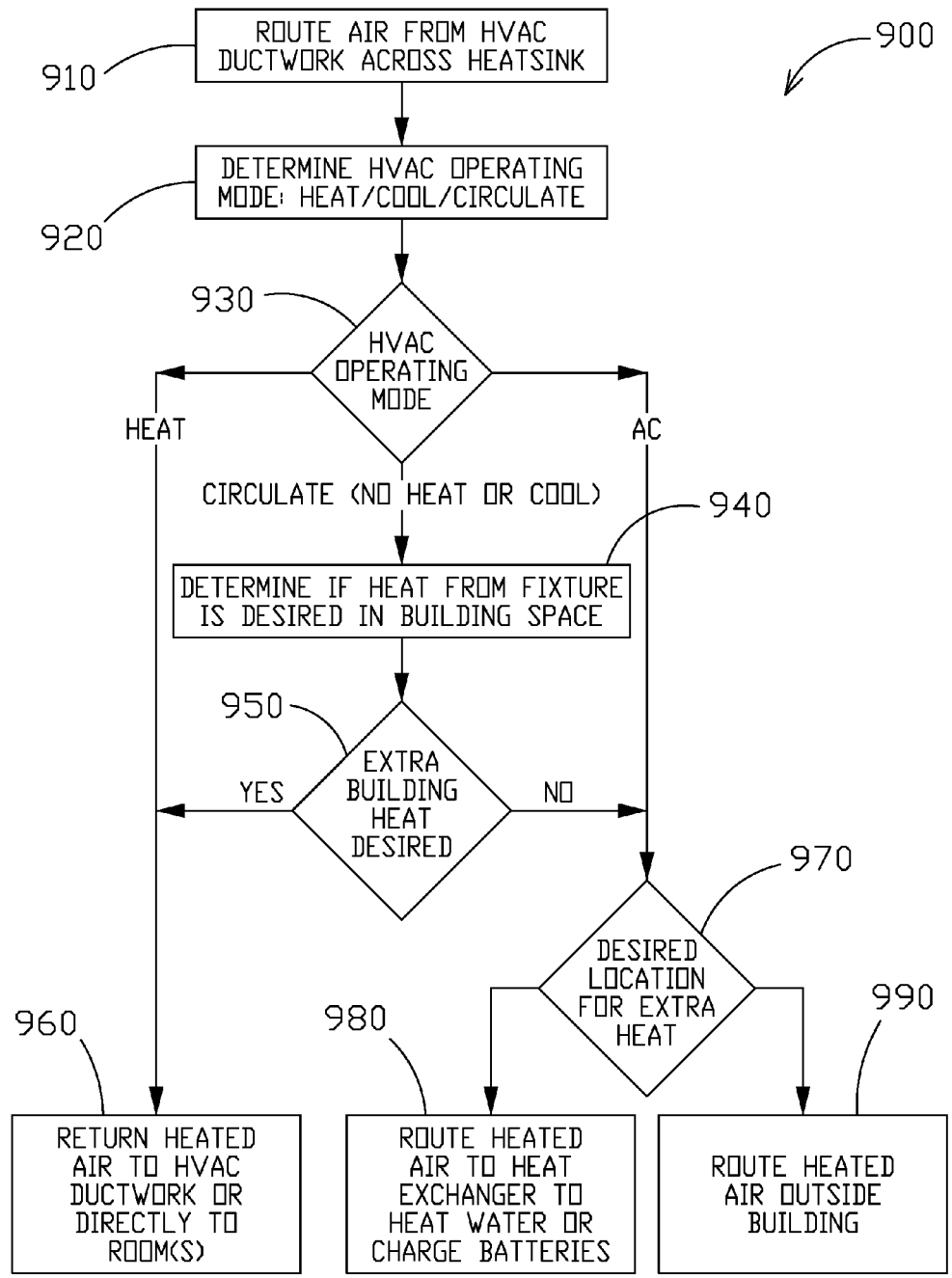
FIG. 9 is a flow diagram illustrating a method of operating an LED cooling system in accordance with some embodiments of the present invention.

One method uses a monitoring system to determine appropriate operating strategies for a system according to embodiments of the present invention. FIG. 9 is a flow diagram illustrating a method 900 of operating an LED cooling system in accordance with some embodiments of the present invention. Some embodiments of method 900 can be applied to the building as a whole or to portions of a building (e.g., rooms, floors, or other fabricated zones). As shown in FIG. 9, monitoring operation 920 monitors the status of an HVAC system that can supply heated air, air-conditioning, and/or ventilation within a building. In accordance with some embodiments, monitoring operation 920 can be done by determining the control setting (e.g., heat, cool, or fan only) of an HVAC system. In some embodiments, monitoring operation 920 monitors the inside temperature and/or the temperature of the airflow through the HVAC ductwork. Decision operations 930, 950, and 970 then determine the routing of the heat from the lighting system. In some embodiments, valves within fluid conduits are controlled by one or more actuators. These valves can be automatically opened or closed to route heat to or from the HVAC system. A control sub-system can operate the actuators on instruction from the monitored status.

In some embodiments, regardless of HVAC operating mode, air is drawn from the HVAC ductwork and passed across one or more heat sources (e.g., heat sinks) increasing the thermal energy of the air per operation 910. If a determination is made that the HVAC system is currently supplying heat, then decision operation 930 can route the heated air from the heat source back to the HVAC ductwork (or if so designed, directly to a room).

In the case that the HVAC system is circulating air but neither supplying heating or cooling, monitoring/processing operation 940 determines if additional heat from fixture is desired in building space. This might occur when temperatures were at the minimum HVAC thermostat, but when some additional heat would be desired. (For instance, the HVAC system might be designed to heat a building to 68° F. for winter, but occupants might desire a higher temperature for greater comfort. Conversely, in the summer, the building might be at or below the air conditioning set point of 72° and additional heat would not be desired.) Decision operation 950 then decides what to do with the heated air from the light fixtures. The heated air can be returned to the HVAC ductwork in HVAC routing operation 960.

If not routed to the HVAC system per operation 960, or if monitoring operation 920 determines the HVAC system is currently supplying air-conditioning, decision operation 970 can route the heated air to a heat exchanger to store the energy (e.g., in an electrical energy storage system, e.g., 760/770, FIG. 7B, or to a water heating system, e.g., e.g. 780, FIG. 7B) in storage routing operation 980, or routed externally to the building or to one or more rooms or zones in venting routing operation 990. In some embodiments, one or more decision operations may be controlled by a master control system used by building administrators.

Additional Thermal Systems—Variations

Solid-state lighting and/or other electrical/electronic components can also be used outside. One example of a location of solid-state lighting used outside is outdoor sporting venues such as football, baseball, and soccer fields. The lighting fixtures in these venues are typically exposed to naturally occurring weather conditions and are without the protection and climate control provided to lighting fixtures within buildings. As such, adequate heat rejection in outside venues can be difficult especially when a collection of solid-state electronics is highly concentrated or when ambient temperatures are high.

Solid-state sports lights on high poles are an example of a situation in which providing adequate ambient heat sinking capability can be difficult due to the given the requirements for construction many feet in the air. Without adequate heat rejection, the lighting and other electrical/electronic components are not able to perform at a peak performance. Furthermore, the lack of adequate heat rejection may result in damage to the lighting and/or other electrical/electronic components.

FIGS. 10-14 illustrate various examples of systems using circulating fluid in contact with thermal masses or with remotely mounted heat sinks to accept heat rejected by one or more heat sources. Examples of thermal masses include, but are not limited to, the ground and structures with remotely mounted heat sinks. One example of a system that may use circulating fluid in contact with thermal masses or with remotely mounted heat sinks is outdoor solid-state lighting with the lighting sources being mounted on tall poles (e.g. wide area lighting such as a parking lot, street lighting, sports venue lighting, etc.) as illustrated in FIGS. 10-14.

Some embodiments can use either existing or new heat transfer systems to remove heat from lighting fixtures. In addition, calculations regarding the characteristics of the heat rejection needed to adequately dissipate heat from the lighting fixture can be used to design the heat rejection system. In a LED lighting fixture, for example, a calculation can be made of the expected heat energy rejection that will be needed based on wattage of the light source and known or estimated thermal efficiency/luminous efficacy. In addition, weather and environmental factors (e.g., average temperature, ground conditions, etc.) can be included in the calculation.

Using the characteristics of the light source and other factors, the calculated heat energy rejection can then be correlated to known thermal transfer characteristics of ground or thermal mass heat absorption systems (e.g., geothermal heating/cooling installations). For example, these calculations can be used in determining the type of coolant, the length of tubing in contact with the thermal mass, the type of tubing, and/or other properties of the heat absorption system. These calculations will typically vary with each installation (e.g., at different locations, different lighting fixtures, etc), but are considered a normal part of heat absorption system calculations. Variations are within the skilled artisan's skill.

Eighth Additional Embodiment

Figure 10:
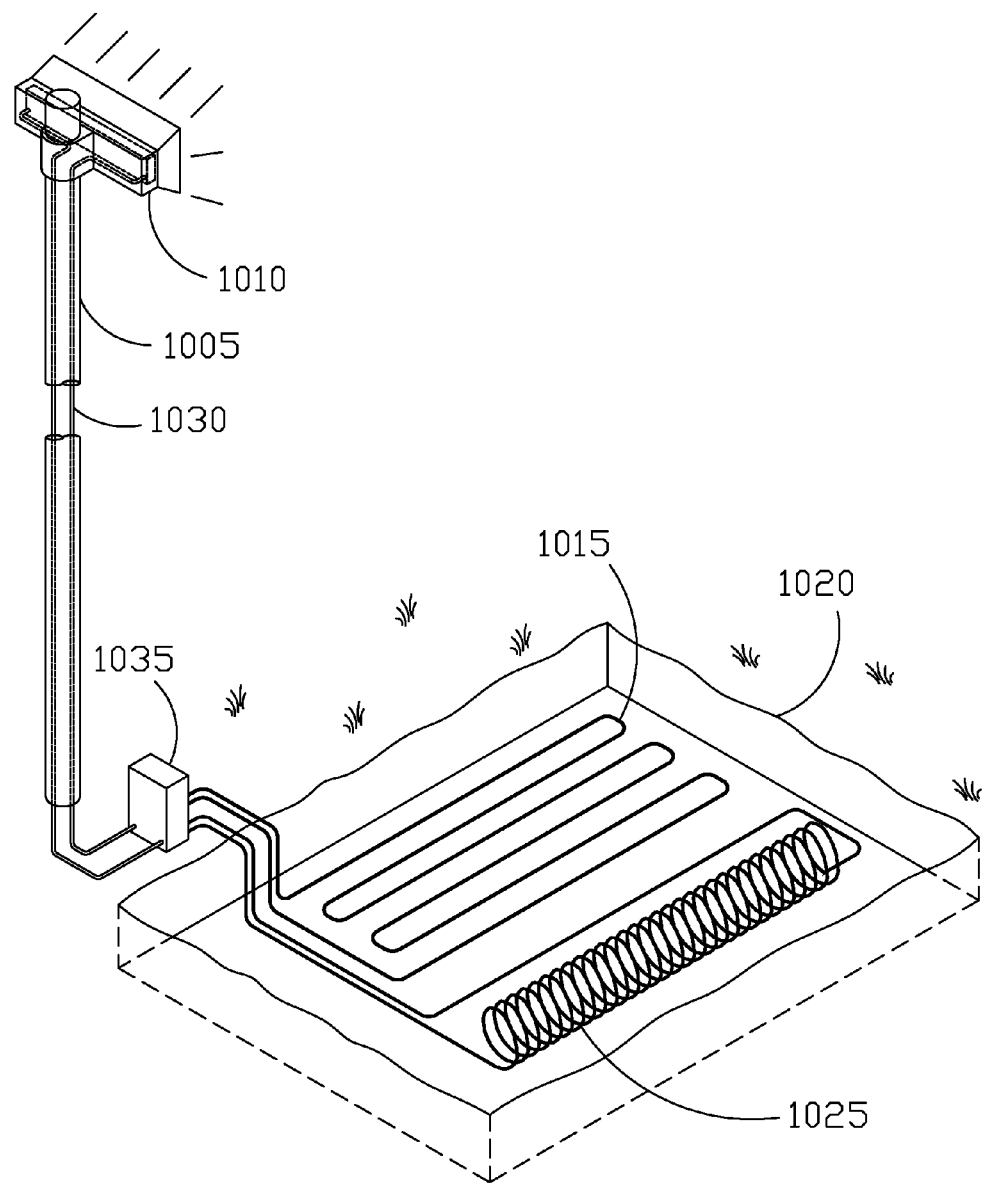
FIG. 10 shows an example of an outdoor pole with a solid-state lighting fixture using a ground cooling loop in accordance with some embodiments of the present invention.

FIG. 10 shows an outdoor pole 1005 with solid-state lighting fixture 1010 using ground cooling loop 1015 in accordance with some embodiment of the present invention. In the embodiments illustrated in FIG. 10, ground cooling loop 1015 is installed in a location in contact with a suitable mass (e.g., under ground). The heat transfer from the heat source within lighting fixture 1010 can be done in a variety of ways. For example, lighting fixture 1010 can be one of the lighting fixtures described in FIG. 2A, 3A, 4 or 5A-E and circulating fluid can be used to remove the heat in accordance with the lighting fixture design. In some embodiments, the circulating fluid can be in direct contact with the heat source or heat sink, or one or more separate loops can be used to transfer heat from the fixture to a heat exchanger that transfers heat to the ground cooling loop. In addition, heat pipes, extended heat sinks, or other known or commercially available mechanisms can be used to transfer heat from the LED light source or power source.

Ground cooling loop 1015 is located in trench 1020 which can be narrow (slot type) or wide and open. Trench 1020 can be on the order of one to ten feet deep in order to sufficiently place the tubing in contact with the ground. In some embodiments, trench 1020 for cooling loops 1015 and 1025 can be approximately tens of feet to hundreds of feet long. However, other embodiments envision shorter and longer lengths as wells as deeper and shallower depths for trench 1020. In addition to trench 1020, some embodiments of the present invention use other types of thermal masses such as, but not limited to, a deep well, shallow well, a pond or a lake, a structure such as metal seats or bleachers (e.g. such as associated with athletic fields), a shallow bury to created a field heating grid, concrete structures, and others.

In accordance with some embodiments of the present invention, the tubing used in ground cooling loop 1015 can include but not be limited to polyethylene, polybutylene, other polymer, copper, aluminum, other metals, or any other type of tubing suitable for pressures, temperatures, and ground conditions. In addition to a variety of tubing materials, ground cooling loop 1015 can be formed into a variety of different shapes. For example, the tubing may be buried relatively straight relative to trench 1020, or may be installed in coils 1025 or with other variations to provide greater ground contact per foot of trench. The designer with skill in the relevant arts would know the features to consider.

In some embodiments, radiators and/or heat sinks that can be cooled by ambient air or forced airflow can also be used as a method of heat transfer from the heat source associated with lighting fixture 1010 to tubing 1030. Pump 1035 can be used to circulate fluid through ground loop 1015 and/or tubing 1030. In some embodiments, the fluid is pumped through tubing 1030 in pole 1005 to cool lighting fixture 1010 before being returned to ground loop 1015 to be cooled. In accordance with some embodiments of the present invention, a variety of pumps may be selected based on appropriate circulation requirements (e.g., total flow required, distance and height, duty cycle, and other requirements). For example, a small installation with a low anticipated duty cycle might use a fractional horsepower centrifugal type pump. In contrast, a large installation with very tall poles might require a multiple horsepower jet or positive displacement pump.

Ninth Additional Embodiment

Figure 11B:
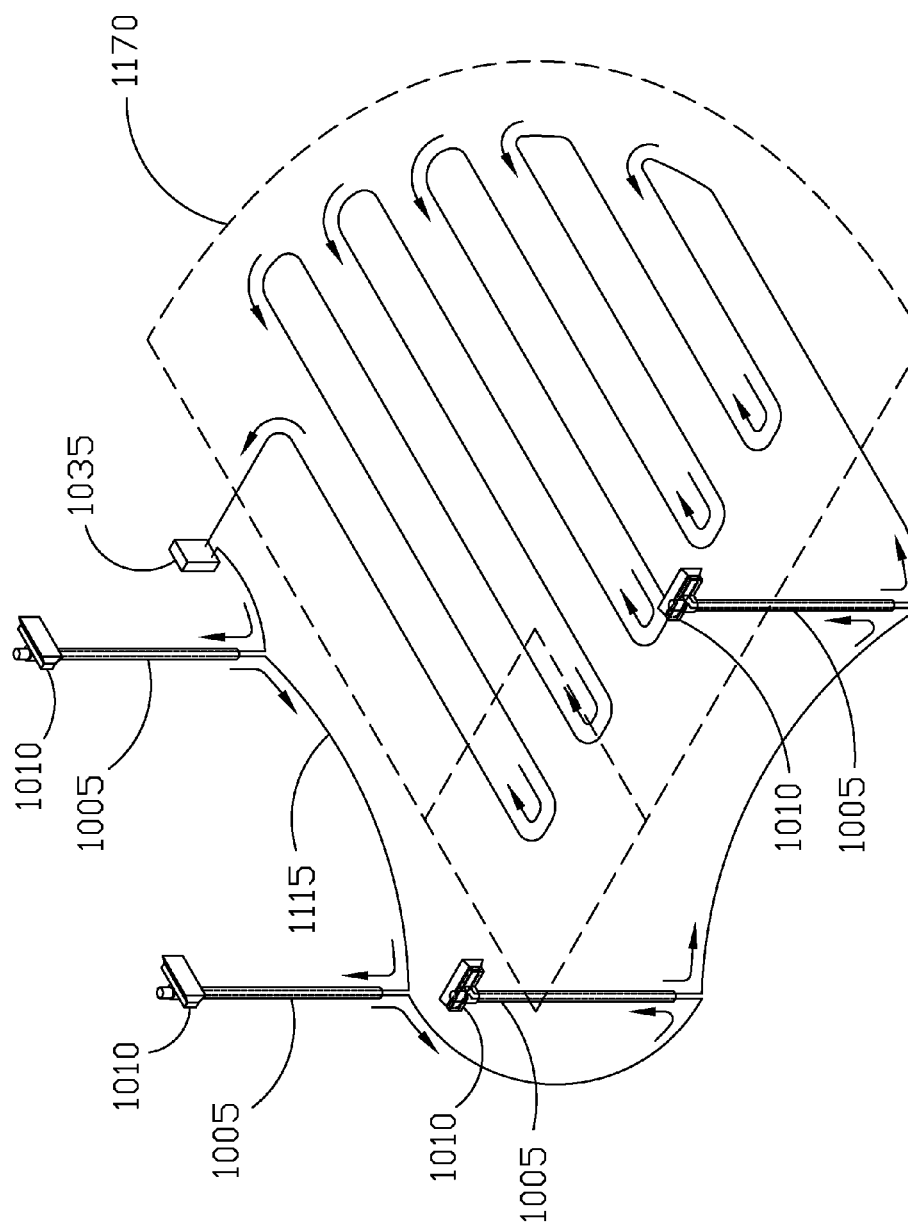

FIGS. 11A-11C illustrate various examples of configurations for multiple solid-state lighting systems using circulating fluid that may be used in accordance with some embodiments of the present invention. In some situations, closely grouped poles or other structures may not have sufficient ground or thermal mass available in close proximity to provide sufficient heat rejection to the lighting sources. As a result, some embodiments of the present invention allow multiple poles or structures to be cooled by series or parallel loops of fluid before the fluid is routed (e.g. by pump 1035) to the thermal mass.

FIG. 11A shows multiple outdoor poles 1005 with solid-state lighting fixtures 1010 using ground cooling loop 1115. More specifically, FIG. 11A shows multiple poles 1005 located around field 1165 (e.g., football field, tennis courts, or other) that are interconnected connected with ground cooling loop 1115. As illustrated, fluid travels in series from one pole through the ground to the next pole.

In some embodiments, the fluid can be distributed to multiple poles in series or parallel and then travel to one or more ground cooling loops. FIG. 11B shows an installation wherein the fluid is distributed to multiple poles 1005 in series by a first ground cooling loop 1115 and then to a second thermal cooling loop 1170. FIG. 11C shows a similar installation wherein fluid could be distributed to multiple poles 1005 in parallel via loop 1115 and then to thermal cooling loop 1170. FIG. 11D shows a similar installation wherein fluid alternates in series between cooling loop 1115 and poles 1005. The examples illustrated in FIGS. 11A-11D are meant to be illustrative of the types of configurations that may be used in accordance with embodiments of the present invention. Many other configurations of fluid circulation systems are possible in accordance with some embodiments of the present invention.

Tenth Additional Embodiment

Figure 12:
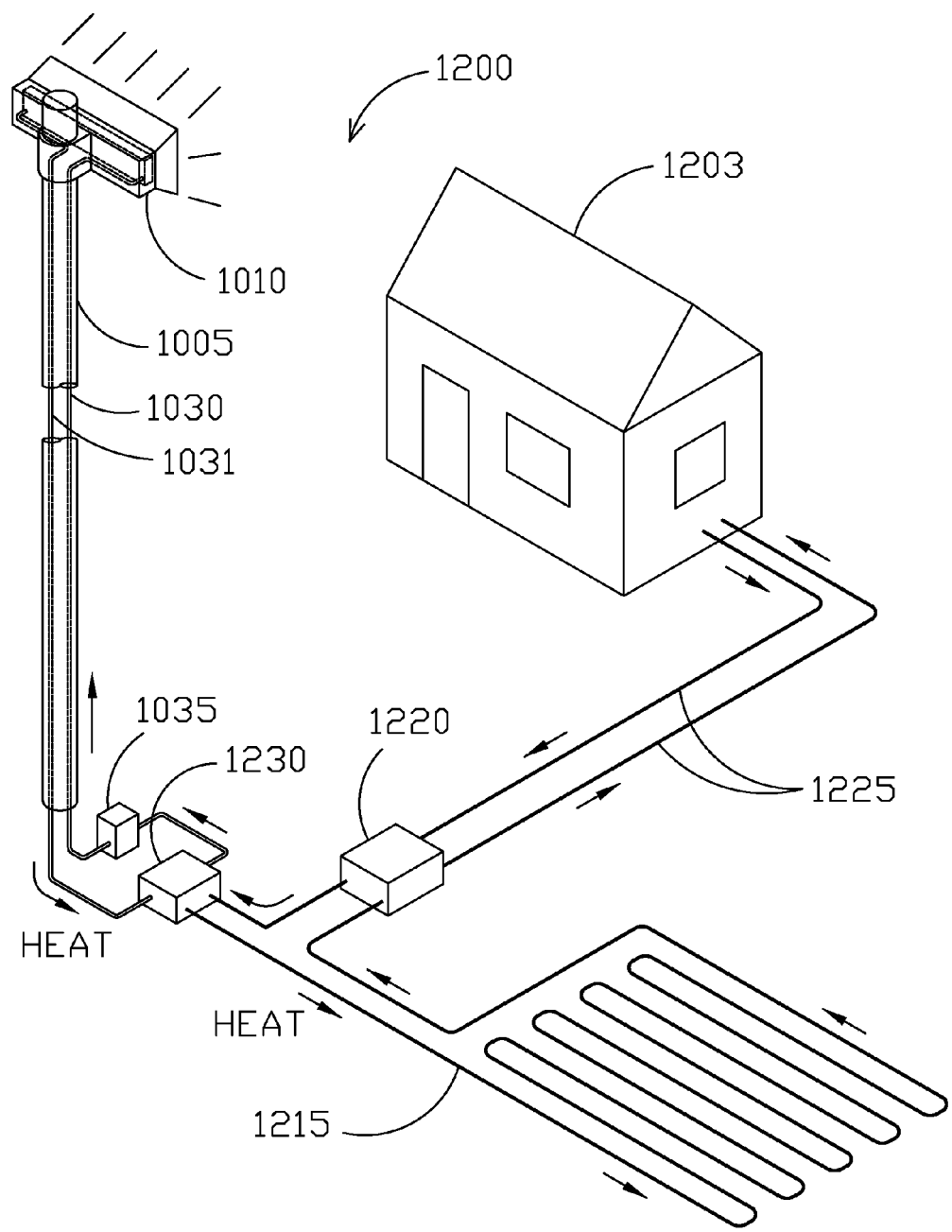
FIG. 12 illustrates an example of a solid-state lighting system using circulating fluid that transfers heat to a geothermal loop connected with a building HVAC system that may be used in accordance with some embodiments of the present invention.

FIG. 12 illustrates an example of a solid-state lighting system 1200 using circulating fluid that transfers heat to a geothermal loop 1215 connected with a building 1203 HVAC system that may be used in accordance with some embodiments of the present invention. In the embodiments illustrated in FIG. 12, circulating fluid transfers heat to a geothermal loop 1215 that is connected with a building HVAC system exemplified by heat pump or other mechanism 1220. Heat pump or other mechanism 1220 is connected to the building 1203 through refrigerant or other fluid lines 1225.

Fluid is circulated in pole loop up tube 1030 and down tube 1031 by pump 1035 and is routed to heat exchanger 1230 that results in a transfer of the heat to fluid in the geothermal loop 1215 before the fluid has circulated through ground. This cools lighting fixture 1010 and transfers heat to the ground loop instead of directly to the fluid input to the heat pump 1220.

Eleventh Additional Embodiment

Figure 13:
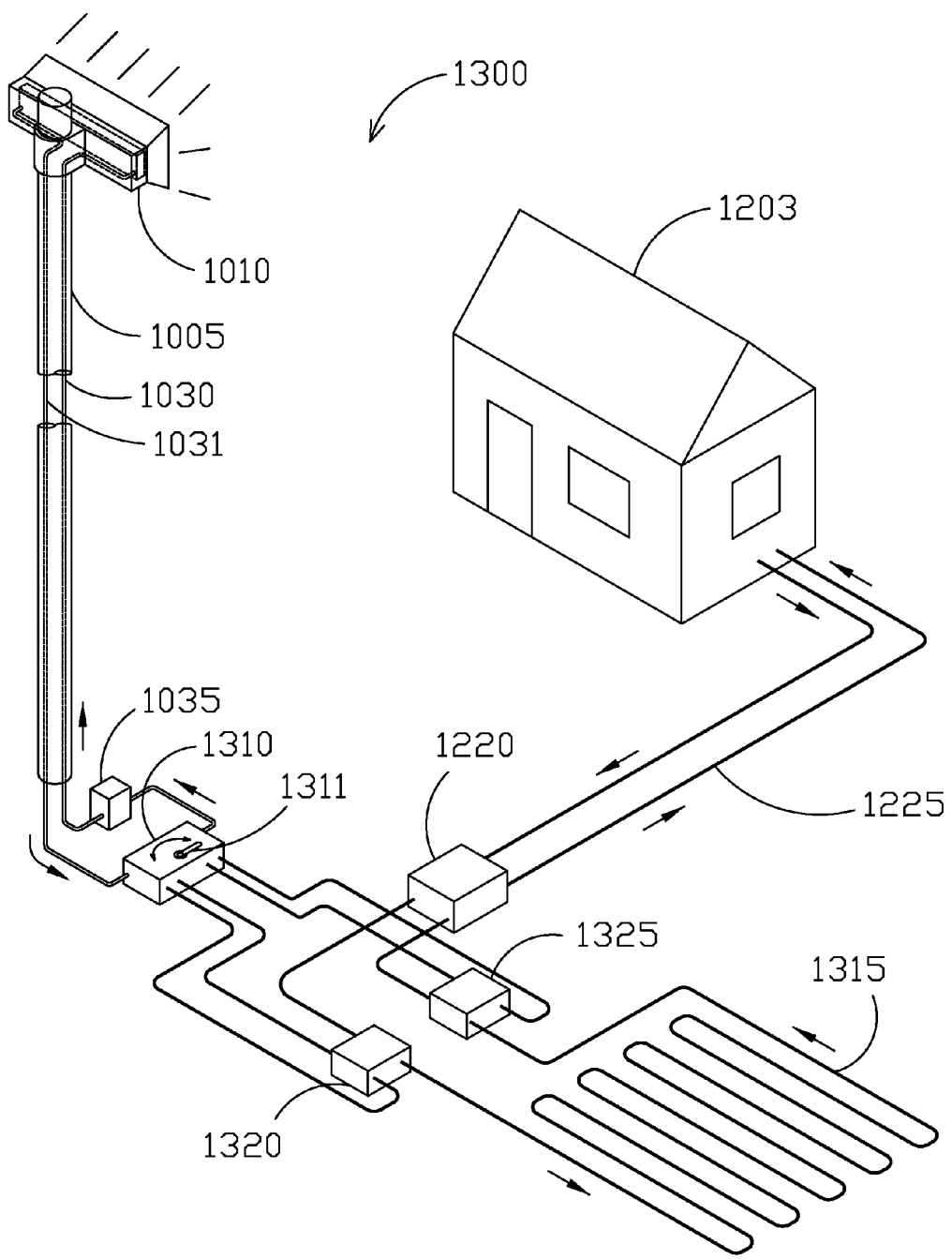
FIG. 13 illustrates an example of a solid-state lighting system that allows an operational change (e.g. switch between heating or cooling functions) to occur in accordance with some embodiments of the present invention.

FIG. 13 illustrates an example of a solid-state lighting system 1300 that allows an operational change to occur in accordance with some embodiments of the present invention. Some embodiments of the present invention allow for an operational change of the solid-state lighting system depending on whether the building needs heating or cooling. During an indoor heating cycle, for example, fluid from pole loop 1030/1031 is routed to heat exchanger 1310 and transfers heat to fluid in the geothermal loop 1315 through either heat exchanger 1320 or 1325. This cools the fixture while at the same time adding useful heat to the building system. During an indoor cooling cycle, the fluid from pole loop 1030 is routed to heat exchanger 1320 and transfers heat to fluid in the geothermal loop 1315 before the fluid has circulated through the ground. This cools the fixture and transfers heat to the ground loop instead of directly to the fluid input to the heat pump. During an indoor heating cycle, the fluid from pole loop 1030 is routed to heat exchanger 1325 and transfers heat to fluid in the geothermal loop 1315 after the fluid has circulated through the ground. This cools the fixture and transfers heat directly to the fluid input to the heat pump instead of to the ground loop. A switch 1311 (manually operated or electrically or electronically actuated) can control which heat exchanger path is used.

Twelfth Additional Embodiment

Figure 14:
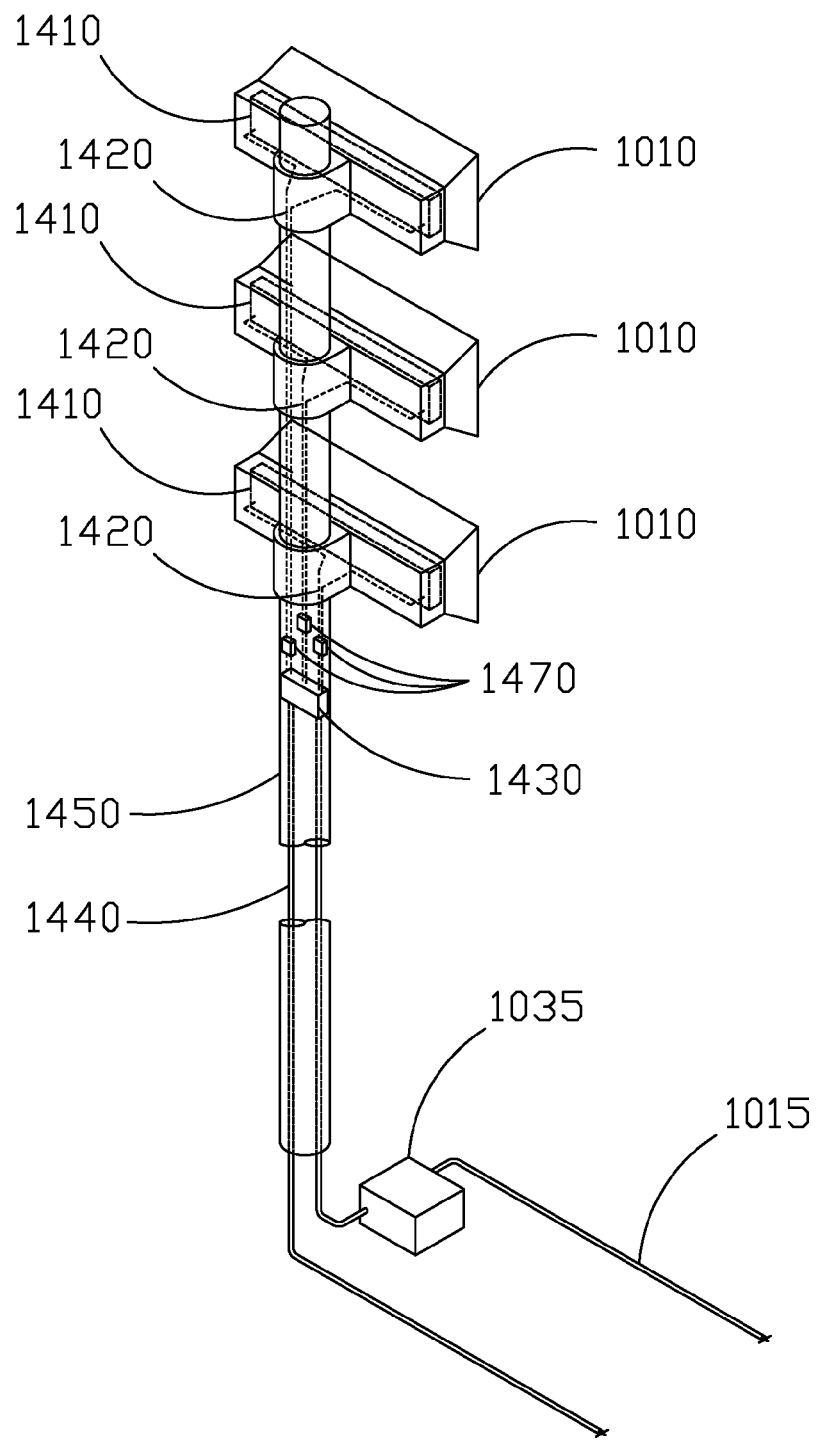
FIG. 14 illustrates an example of a lighting pole with multiple heat exchangers which are able to remove heat from one or more heat source in accordance with some embodiments of the present invention.

FIG. 14 illustrates an example of a lighting pole 1450 with multiple lighting fixtures in accordance with some embodiments of the present invention. As illustrated in FIG. 14, each lighting fixture 1010 can include an individual heat exchanger 1410 that is able to remove heat from one or more heat source within the lighting fixture. Heat exchangers 1410 provide thermal communication between the one or more heat sources within the lighting fixtures and one or more heat transfer components 1420 (e.g. tubing, heat pipes, etc.). In some embodiments, the heat transfer component is tubing that can be connected to pump 1470 for circulating the fluid between heat exchanger 1430 and heat exchangers 1410. In some embodiments, heat transfer components 1420 are thermally connected to heat exchanger 1430 that is in thermal communication with tubing 1440 that can include one or more ground loops or connections to heating/cooling systems. Pump 1035 can be used in accordance with some embodiments to force the fluid through tubing 1440 to heat exchanger 1430 and through ground cooling loop 1015.

Thirteenth Additional Embodiment

Figure 15A:
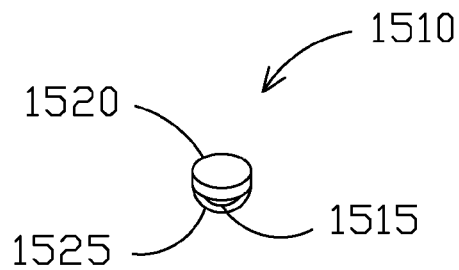
FIGS. 15A-15D illustrate various components of a lighting fixture that may be used in accordance with some embodiments of the present invention.

FIGS. 15A-15D illustrate various components of a lighting fixture that may be used in accordance with some embodiments of the present invention. In particular, FIG. 15A represents an example of an LED assembly 1510 that may be used in some embodiments of the present invention. According to the embodiments shown in FIG. 15A, LED assembly 1510 includes LED chip 1515, die/heat sink 1520, and lens 1525. In the embodiments shown in FIG. 15A-D, the LED chip 1515 is located on a silicon submount. Because LEDs can be subject to thermal degradation, die/heat sink 1520 can be used to dissipate the heat generated by the LED chip 1515 and the silicon submount (not shown, but well known in the art). Typically, a bond wire (not shown) connects the silicon submount to a cathode lead that is used to provide power to LED chip 1515. In some embodiments, LED assembly 1510 may include an outer packaging (not shown but well known in the art) to protect various components and to direct the dissipation of heat from heat sink 1520. In some embodiments lens 1525 can be attached directly to the outer packaging.

Figure 15B:
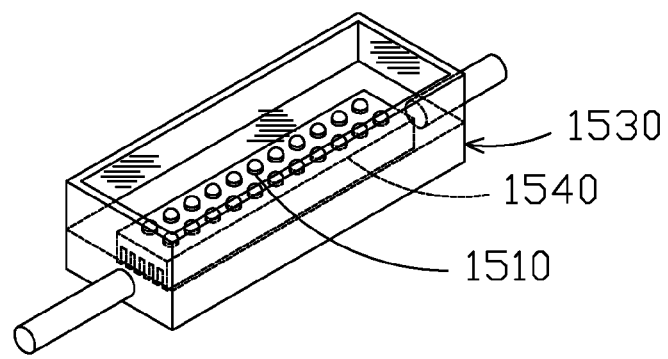
Figure 15C:
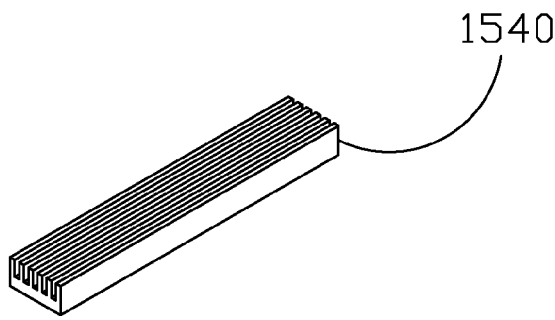
Figure 15D:
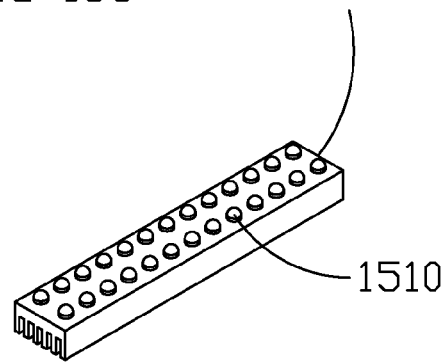

FIG. 15B illustrates an example LED fixture 1530 (shown facing up, but could be oriented in any direction). This fixture is similar to the lighting fixtures described in FIGS. 2A, 3A, 4, and 5A-E, but could be different in not having a lens structure as previously described, or could have other differences from the previous fixtures, particularly of the type that would be appropriate for installation in an outdoor or industrial setting. Said fixture can be used in various embodiments of pole lighting (e.g., FIGS. 10, 11A-D, 12, and 13). Fixture 1530, FIG. 15B can be populated with one or more LED assemblies 1510 and heat sinks 1540 (FIG. 15A-15B) where the heat sink 1540 can be located in a section of fixture 1530 to allow additional fluid to flow by a conduit into a space in section 1530, over and by heat sink 1540, and out a conduit on the opposite side of section 1530 and extract the heat (e.g. like FIGS. 2A, 3A, 4, and 5A). FIG. 15C shows an example of a heat sink that could be included in fixture 1530. FIG. 15D shows the underside of heatsink 1540 with LEDs 1510 mounted on the heatsink.

Various systems and methods can be used to interface fixture 1530 with a fluid transfer conduit. Examples include, but are not limited to, slip-fit tubing, extended flanges, pipe nipples, etc.

Fourteenth Additional Embodiment

Figure 16A:
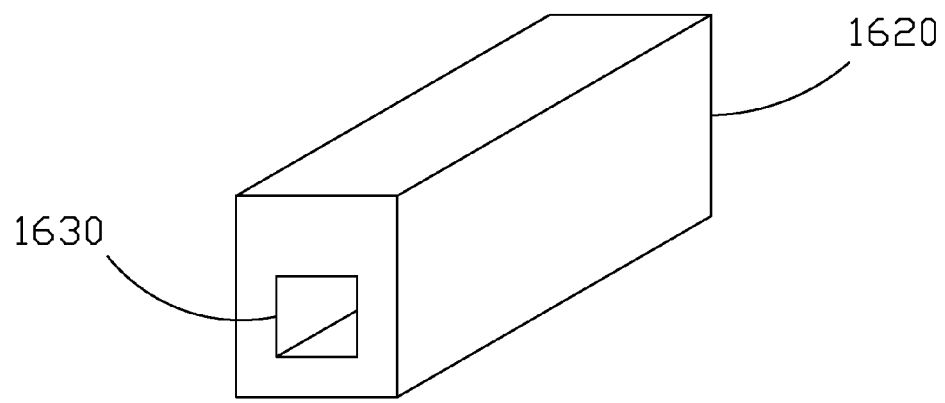
FIGS. 16A-16E illustrate various lighting fixtures and components that may be used in accordance with some embodiments of the present invention.
Figure 16B:
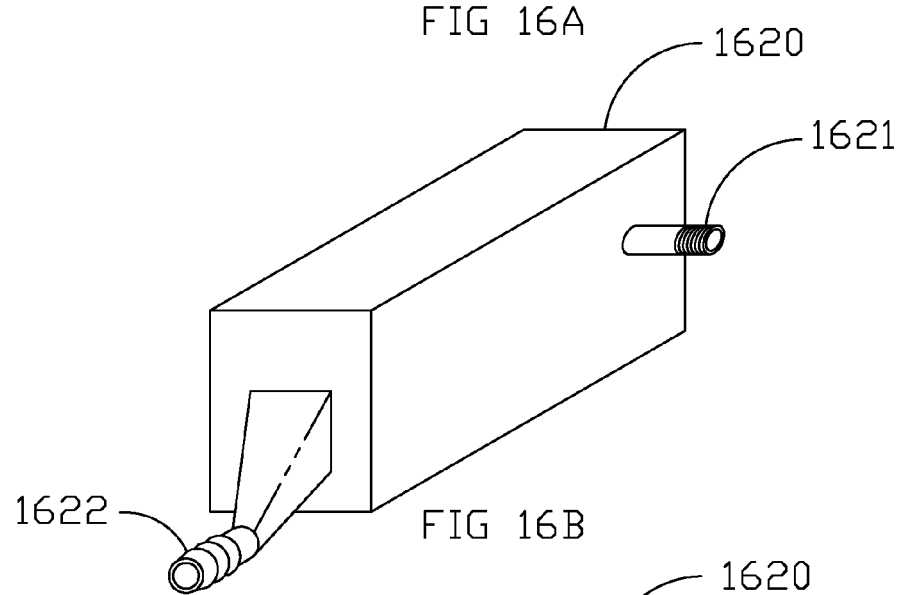
Figure 16C:
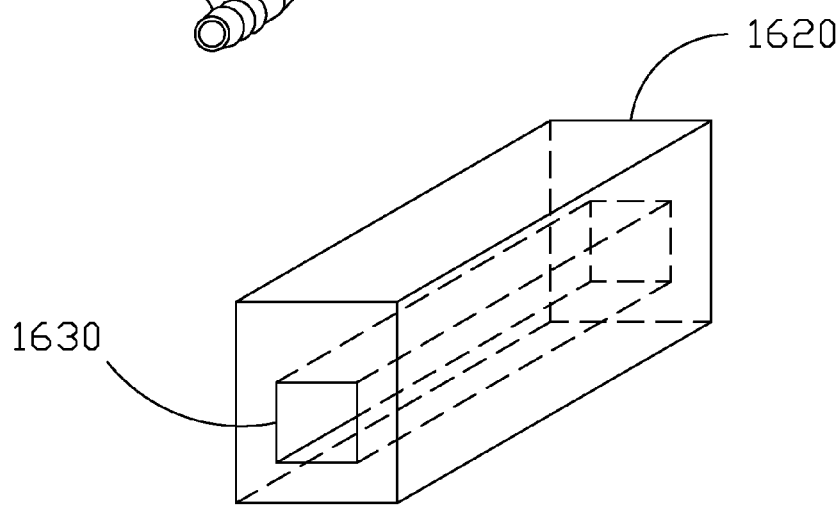
Figure 16D:
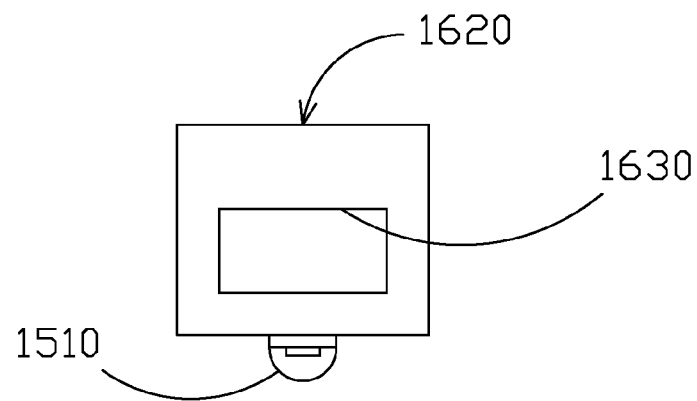
Figure 16E:
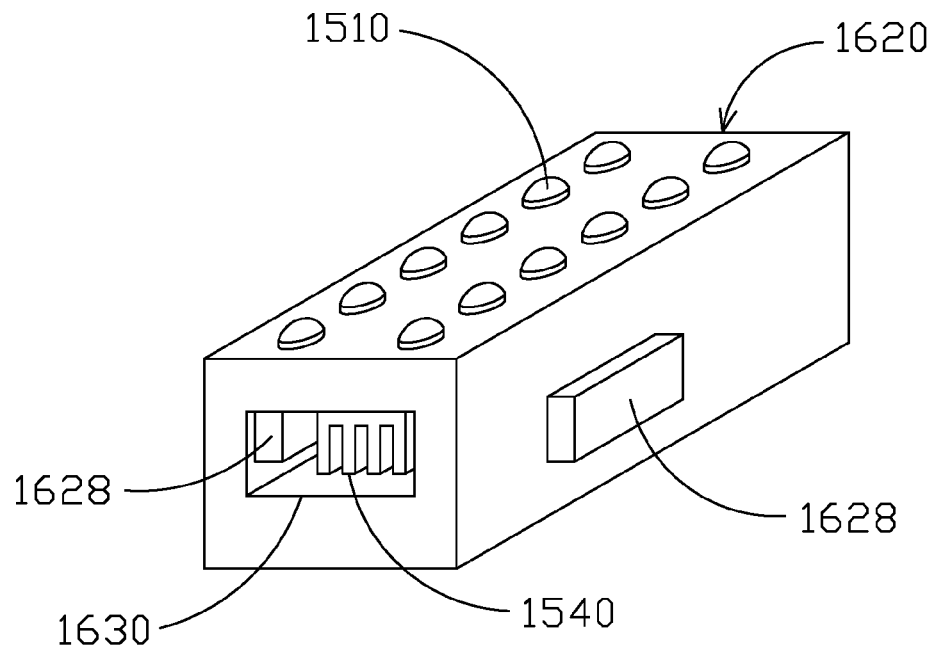

FIGS. 16A-16E illustrate various lighting fixtures and components that may be used in accordance with some embodiments of the present invention. In particular, FIG. 16A shows an example of a lighting fixture 1620 that can be used in some embodiments of the present invention. As illustrated in FIG. 16A-E, lighting fixture 1620 includes a mounting location for LEDs 1510. As illustrated in FIG. 16D-E, LEDs could be mounted to fixture 1620 by various means that would affect heat transfer from the LEDs 1510 to the fixture 1620. This would typically involve close physical and thermal contact between the LEDs 1510 and the fixture 1620, as seen in FIG. 16D. Thermal gel, paste, or grease could be used to improve heat transfer as is well known in the art. The LED assembly could be secured by means of threaded fasteners, adhesives, bayonet type mountings, rivets or deforming fasteners, friction or compression mounting in dovetail or T-slots. Additionally, individual LEDs or groups of LEDs could be affixed to a thermally conductive substrate or heat sink, such as a copper or aluminum plate or sheet, which could then be attached to the fixture using thermally conductive means as previously discussed. Or, the mounting surface of fixture 1620 could be machined to include bosses or extrusions which could be used to thread or stake the LED assembly to the fixture. Many other mounting methods are possible as well. FIG. 16A illustrates passage 1630 that allows fluid to travel within the apparatus. FIG. 16B illustrates how lighting fixture 1620 can be configured to interface with a fluid transfer conduit in a fluid heat exchange system as illustrated in FIGS. 10, 11A-D, 12, 13, and 14. For example a tube 1622 could be installed at each end of fixture 1620 which could be connected to a fluid transfer conduit by slip fitting, threaded fittings, quick couplers, compression fittings, hose barbs, etc. Similarly, a standard pipe nipple 1621 might be installed to connect by pipe thread to a fluid conduit system. Other types of connections could be used as well.

FIG. 16C illustrates lighting fixture 1620 with passage 1630 in hidden lines. In accordance with some embodiments, a heat sink can be used within passage 1630 or the heat sink can be formed as an integral part of fixture 1620. Various methods known to those having ordinary skill in the art could be used to interface fixture 1620 with a fluid transfer conduit, such as slip-fit tubing, extended flanges, pipe nipples, etc.

FIG. 16D shows an end view of lighting fixture 1620 illustrating placement of one or more LED assemblies 1510 in accordance with some embodiments of the present invention. As shown in the embodiments of FIG. 16D, LED assembly 1510 may be placed externally to the lighting fixture with the heat source(s) associated with the LED assembly being located at or within the lighting fixture. FIG. 16E shows a lighting fixture 1620 with LEDs attached externally. In accordance with some embodiments, these LEDs can be affixed so that the heat generated by the associated heat source(s) is conducted to fixture 1620, and can removed by circulation of a fluid through the fixture. In some embodiments, the fluid circulating through the fixture may interface with individual heat exchanger 1540, FIG. 14.

According to some embodiments, heat sink 1540 can be thermally connected to one or more LEDs or to fixture 1620 to increase thermal transfer. Electronics driver 1628 can be included within passage 1630 in some embodiments of the present invention. In other embodiments, electronics driver 1628 may be mounted externally to lighting fixture 1620. In either case, lighting fixture 1620 might be used to cool driver 1628 either combined with or separate from LEDs 1510 being mounted on lighting fixture 1620.

Sample Heat Load Calculations

The process of transferring heat from a stationary aluminum heat sink to moving air or other fluids by forced convection is well known in the art. Further, methods of calculation, constants, and coefficients are well-known for many materials, of which air and aluminum are only examples.

The process known generally in the industry as forced or assisted convective heat transfer takes place both by diffusion of heat from molecule to molecule (especially near a stationary surface where fluid velocity is low) and by bulk movement of air molecules from one location to another. The bulk movement of air is created by an external force such as a fan, impeller, or pump.

Calculations of this type are well known to those in the heating and cooling arts, as illustrated for example in the standard text *Thermodynamics and Heat Power, Seventh Edi-*

*tion* by Irving Granet and Maurice Bluestein (Pearson/Prentice Hall, Upper Saddle River, N.J., 2004, ISBN 0-13-110672-4).

The equation for convection can be expressed as:

$$q = hA\Delta T \quad (1)$$

where
- q=heat transferred per unit time (W)
- A=heat transfer area of the surface ($m^2$)
- h=convective heat transfer coefficient of the process ($W/m^{2\circ}$ C.)
- $\Delta T$=temperature difference between the surface and the bulk fluid (K or ° C.)

The convection heat transfer coefficient, h, is dependent on the type of heat transfer medium, its physical state (vapor or liquid), its flow properties such as velocity, viscosity and other flow and temperature dependent properties.

In general the convective heat transfer coefficient for air and water at some common flow rates is within the ranges:

$$\text{Air:} 10\text{-}100 (W/m^{2\circ} \text{ C.})$$

$$\text{Water:} 500\text{-}10{,}000 (W/m^{2\circ} \text{ C.})$$

An interior lighting system designed according to aspects of the present invention, could have on the order of 20 LEDs per fixture. Each LED would dissipate 1 watt with a resultant heat dissipation of 20 watts per fixture. For this fixture, air at 20° C. is ducted to flow over the surface of a common finned aluminum extruded heat sink for the fixture. The heat sink measures approximately 15×15×9 cm and has a useful surface area of 0.75 $m^2$. Maintaining the temperature of the surface of the heat sink at 50° C. or below could be adequate for LED longevity and performance.

For this arrangement, assume a conservative 10 $W/m^{2\circ}$ C. dynamic heat transfer coefficient based on an air flow of 0.125 $m^3$/min or 0.75 $m^3$/hr (=approximately 0.15 kg/hr mass flow of air) and a 30° C. temperature difference. Under these conditions, $$10 \, W/m^{2\circ} \, C. \times 30° \, C. \times 0.75 \, m^2 = 22.5 \text{ watts}$$

which is more than the required 20 watts per fixture.

A room measuring 25 feet by thirty feet might have 15-30 such fixtures. Assuming 30 fixtures, the heat load for the fixtures would be 30 W times 20 fixtures, or 600 W. The required airflow would be 0.125 $m^3$/min×30=3.75 $m^3$/min, or approximately 130 $ft^3$/min. A furnace putting out 42000 BTU/hr heat such as would be used in a small home typically has an airflow of 800 cfm. Thus an air handler of that size might easily service 6 rooms or a total area of 4500 $ft^2$. Of course these parameters could be adjusted to match different specifications and conditions.

Compared to air, water has approximately 5 times the heat transfer ability per mass flow. Thus for outdoor fixtures having a higher number of LEDs or a higher wattage rating, water cooling would provide much higher heat transfer capability for a given mass flow rate. Assuming 100 W per fixture, a mass flow of 0.125 kg/min., and a 30° temperature differential, cooling would still be adequate, since the 5× power gain would be offset by a 5× increased heat absorption. Thus for a pole having 10 fixtures, a flow of 10×0.125 $m^3$/min=1.25 kg/min or 0.33 gallons per minute would suffice.

The above calculations are illustrative of the types of calculations that would be performed by the system designer to determine appropriate air flow, heat sink size, etc. and are intended to provide a consideration of the factors that would be considered by those skilled in the art. Specific installation conditions would determine the actual numbers and considerations.

A further example of well-known cooling systems include a typical fan and heatsink arrangement for a personal computer. A typical inexpensive fan available for installation is the ARCTIC COOLING "Freezer 7 Pro Rev.2 92 mm Fluid Dynamic CPU Cooler" available commercially from NewEgg.com (NewEgg.com, 9997 E. Rose Hills Road, Whittier, Calif. 90601). The fan is an axial type, is 92 mm in diameter, and has an operating speed of 900-2500 RPM, and is specified as creating an airflow of 45 CFM (1.25 $m^3$/min), which would be sufficient to cool 10 of the above mentioned 20 watt fixtures. While this type of fan and heatsink is not typical of HVAC cooling system fans, it is illustrative of well-known techniques and equipment for heat transfer.

Additional Embodiments

Hardware or Machine Executable Instructions

Figure 17:
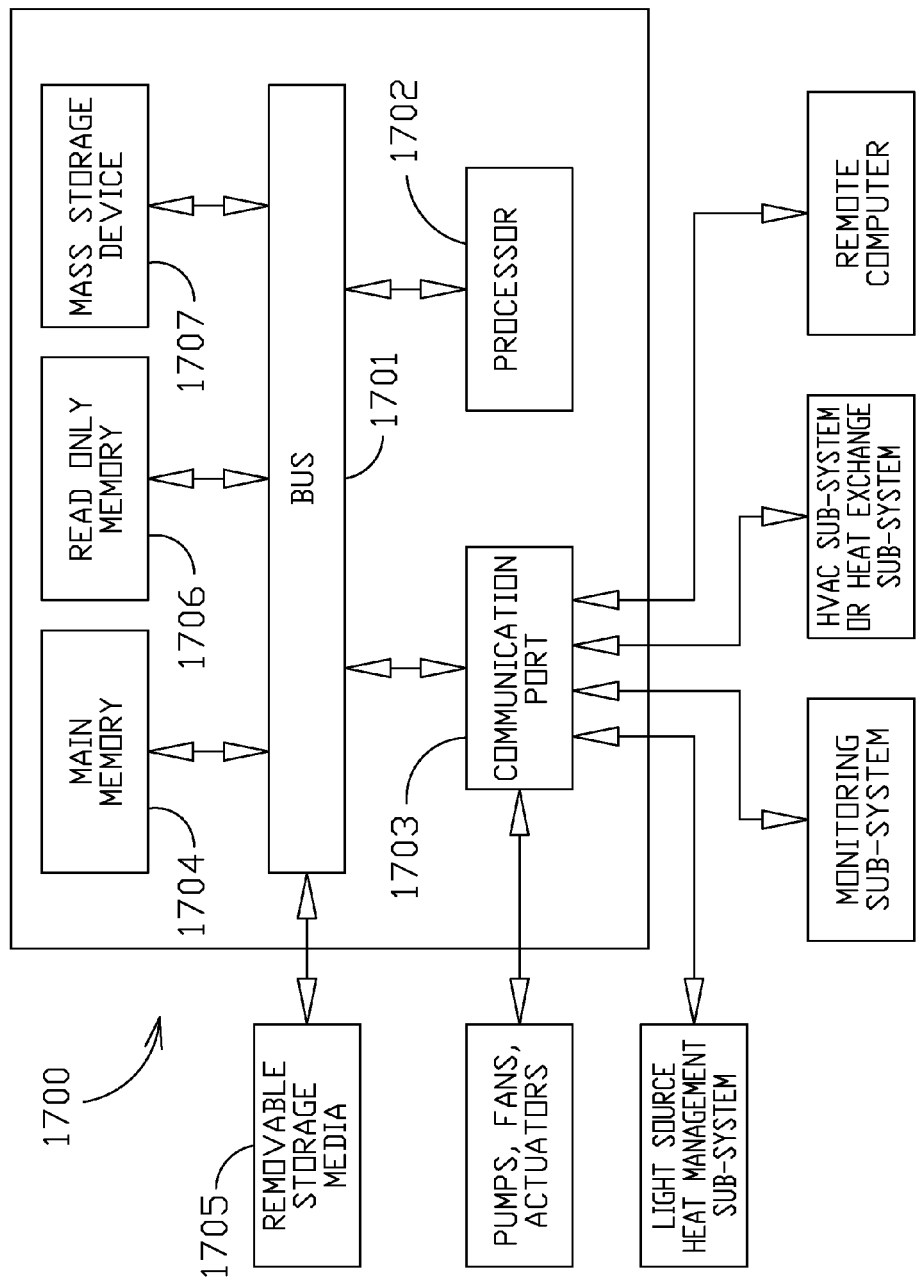
FIG. 17 illustrates an example of a computer system with which some embodiments of the present invention may be utilized.

Embodiments of the present invention include various steps that may be performed by hardware components or may be embodied in machine-executable instructions, which may be used to cause a general-purpose or special-purpose processor programmed with the instructions to perform the steps. Alternatively, the steps may be performed by a combination of hardware, software, and/or firmware. As such, FIG. 17 is an example of a computer system 1700 with which embodiments of the present invention may be utilized. According to the present example, the computer system includes a bus 1701, at least one processor 1702, at least one communication port 1703, a main memory 1704, a removable storage media 1705, a read only memory 1706, and a mass storage 1707.

Processor(s) 1702 can be any known processor, such as, but not limited to, an Intel® Itanium® or Itanium 2® processor(s), or AMD® Opteron® or Athlon MP® processor(s), or Motorola® lines of processors. Communication port(s) 1703 can be any of an RS-232 port for use with a modem based dialup connection, a 10/100 Ethernet port, or a Gigabit port using copper or fiber. Communication port(s) 1703 may be chosen depending on a network such a Local Area Network (LAN), Wide Area Network (WAN), or any network to which the computer system 1700 connects.

Main memory 1704 can be Random Access Memory (RAM), or any other dynamic storage device(s) commonly known in the art. Read only memory 1706 can be any static storage device(s) such as Programmable Read Only Memory (PROM) chips for storing static information such as instructions for processor 1702.

Mass storage 1707 can be used to store information and instructions. For example, hard disks such as the Adaptec® family of SCSI drives, an optical disc, an array of disks such as RAID, such as the Adaptec family of RAID drives, or any other mass storage devices may be used.

Bus 1701 communicatively couples processor(s) 1702 with the other memory, storage and communication blocks. Bus 1701 can be a PCI/PCI-X or SCSI based system bus depending on the storage devices used.

Removable storage media 1705 can be any kind of external hard-drives, floppy drives, IOMEGA® Zip Drives, Compact Disc-Read Only Memory (CD-ROM), Compact Disc-Re-Writable (CD-RW), Digital Video Disk-Read Only Memory (DVD-ROM).

The components described above are meant to exemplify some types of possibilities. In no way should the aforementioned examples limit the scope of the invention, as they are only exemplary embodiments.

FIG. 17 indicates a few examples of sub-systems or other components that could be operably connected to computer system 1700. For example, computer system 1700 could be programmed (directly or remotely) to communicate with and/or instruct such things as:

(a) pumps, fans, actuators, valves, or other components used to move fluid relative a solid-state light source to remove heat of operation of such light sources (see "Pumps/Actuators" box);

(b) monitors, thermostats, status indicators, and other components that provide information relevant to heat management, or use or disposal of heat from operation of solid-state sources (see "Monitoring sub-system(s) box in FIG. 17);

(c) HVAC sub-system components (e.g. diverter valves, fans, gates, etc.) (see "HVAC sub-system" in FIG. 17);

(d) remote devices such as a remote computer (see "Remote Computer" in FIG. 17), which can be used for, inter alia, remote monitoring, programming, data collection, operation instructions, etc.);

(e) other tasks or information gathering related to the disclosed embodiments (see "Light Source Heat Management Sub-System" of FIG. 17).

An example of programming of computer system 1700 is shown in FIG. 9. Examples of monitoring, actuator control, HVAC interface, and other heat management or remote computer tasks are described with the foregoing embodiments. Other tasks are, of course, possible.

One aspect of the invention is that the designer can utilize the general concept of effectively, efficiently, and economically collecting what otherwise is likely waste heat and systematically manage it. The embodiments give a variety of examples. A computer system such as FIG. 17 can be used to facilitate such operations, if desired. The scale of the computer system can vary according to application. For smaller scale applications, there may even be manual controls, or micro-controller(s). For larger scale, full size computers (e.g. PC's, mini-computers, main frames, etc.) might be used.

As can be appreciated by those skilled in the art, the embodiments provide examples of different ways to harvest, so to speak, heat of operation of solid-state light sources (and/or power electronics or other components) in an effective way that can be put to beneficial use(s). One beneficial use is to apply the harvested heat to a dedicated use (e.g. heat a room, building, etc.). Another is to add the harvested heat to another system (e.g. HVAC, geo thermal, etc.). Another is to convert or store the heat for later use (e.g. hot water storage or conversion to stored electrical power).

The skilled artisan can use his/her skills to make design choices for implementing these aspects according to need or desire for each application.

Aspects of the invention apply to single solid-state sources, single fixtures with one or more solid-state sources, or multiple fixtures.

CONCLUSION

In conclusion, the present invention provides novel systems, methods and arrangements for LED heat exhaust management. The components described above are meant to exemplify some types of possibilities. In no way should the aforementioned examples limit the scope of the invention, as they are only exemplary embodiments. While detailed descriptions of one or more embodiments of the invention have been given above, various alternatives, modifications, and equivalents will be apparent to those skilled in the art without varying from the spirit of the invention. Therefore, the above description should not be taken as limiting the scope of the invention, which is defined by the appended claims.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

As an example, the size, configuration, and materials used for the different embodiments can be selected according to need or desire by the skilled artisan for the particular application.

What is claimed is:

1. A system for cooling solid-state lighting fixtures, the system comprising:

a solid-state light source having one or more light-emitting diodes (LEDs) and a heat source, wherein at least a part of the heat source is associated with a heat sink to dissipate heat generated by the heat source;

an enclosure having a plurality of portions with a first portion of the plurality of portions being at least partially transparent and one of the plurality of portions including a fluid transfer conduit interface, wherein the solid-state light source is mounted within the plurality of portions to form two sections of the enclosure that are separated from one another, the LEDs are located in the first section facing the first portion of the enclosure that is at least partially transparent and the heat sink is located in the second section of the enclosure; and a fluid transfer conduit connected to the enclosure via the fluid transfer conduit interface to allow fluid to transport heat generated by the heat source away from the heat sink of the solid-state light source;

wherein the second section of the enclosure encases the heat sink within a heat chamber, and wherein the heat chamber includes inside surfaces and external surfaces with a gap between the inside surfaces and the external surfaces, the inside surfaces are thermally conductive, the external surfaces are thermally insulated, and the fluid is able to flow through the gap between the inside surfaces and external surfaces extracting heat being dissipated by the heat sink.

2. The system of claim 1, wherein a second portion of the plurality of portions includes a vent, the heat sink includes one or more air ducts, and wherein fluid moving through the fluid transfer conduit causes air to be drawn through the vent and across the heat sink and through the one or more air ducts.

3. The system of claim 1, wherein the second section of the enclosure encases the heat sink within a heat chamber that includes an opening to allow the heat chamber to be connected to the fluid transfer conduit.

4. The system of claim 1, wherein the fluid is air or building coolant.

5. The system of claim 1, wherein the fluid transfer conduit is insulated to minimize heat transfer from the fluid inside the fluid transfer conduit to a space external to the fluid transfer conduit.

6. The system of claim 1, wherein the fluid transfer conduit is connected to a fan, a pump, or a blower that forces the fluid through the enclosure.

7. The system of claim 1, wherein the fluid transfer conduit connects multiple solid-state light sources within individual enclosures.

8. The system of claim 7, wherein each of the individual enclosures associated with the multiple solid-state light sources include independently controllable fans to force the fluid across the heat sink associated with the solid-state light source housed within the enclosure.

9. The system of claim 1, wherein the solid-state light source is mounted in a building structure, the fluid transfer conduit is in fluid communication with an outside of the building structure at one end and in fluid communication with the enclosure at another end, and wherein connected to the fluid conduit is a fan, blower, or pump for moving fluid from the outside of the building, through the fluid transfer conduit, and through the enclosure.

10. The system of claim 1, wherein the solid-state light source is mounted in a building structure, the fluid transfer conduit is in fluid communication with an outside of the building structure at one end and in fluid communication with the enclosure at another end, and wherein connected to the fluid conduit is a fan for moving fluid through the enclosure, through the fluid transfer conduit, and to the outside of the building.

11. The system of claim 1, wherein the fluid transfer conduit is coupled to a building heating/cooling system.

12. A system for cooling solid-state lighting fixtures, the system comprising:
- a solid-state light source having one or more light-emitting diodes (LEDs) and a heat source, wherein at least a part of the heat source is associated with a heat sink to dissipate heat generated by the heat source;
- an enclosure having a plurality of portions with a first portion of the plurality of portions being at least partially transparent and one of the plurality of portions including a fluid transfer conduit interface, wherein the solid-state light source is mounted within the plurality of portions to form two sections of the enclosure that are separated from one another, the LEDs are located in the first section facing the first portion of the enclosure that is at least partially transparent and the heat sink is located in the second section of the enclosure; and
- a fluid transfer conduit connected to the enclosure via the fluid transfer conduit interface to allow fluid to transport heat generated by the heat source away from the heat sink of the solid-state light source;
- wherein the fluid transfer conduit connects multiple solid-state light sources within individual enclosures, wherein each of the individual enclosures associated with the multiple solid-state light sources include independently controllable fans to force the fluid across the heat sink associated with the solid-state light source housed within the enclosure.

13. A system for cooling solid-state lighting fixtures, the system comprising:
- a solid-state light source having one or more light-emitting diodes (LEDs) and a heat source, wherein at least a part of the heat source is associated with a heat sink to dissipate heat generated by the heat source;
- an enclosure having a plurality of portions with a first portion of the plurality of portions being at least partially transparent and one of the plurality of portions including a fluid transfer conduit interface, wherein the solid-state light source is mounted within the plurality of portions to form two sections of the enclosure that are separated from one another, the LEDs are located in the first section facing the first portion of the enclosure that is at least partially transparent and the heat sink is located in the second section of the enclosure; and
- a fluid transfer conduit connected to the enclosure via the fluid transfer conduit interface to allow fluid to transport heat generated by the heat source away from the heat sink of the solid-state light source;
- wherein the solid-state light source is mounted in a building structure, the fluid transfer conduit is in fluid communication with an outside of the building structure at one end and in fluid communication with the enclosure at another end, and wherein connected to the fluid conduit is a fan, blower, or pump for moving fluid from the outside of the building, through the fluid transfer conduit, and through the enclosure.

14. A system for cooling solid-state lighting fixtures, the system comprising:
- a solid-state light source having one or more light-emitting diodes (LEDs) and a heat source, wherein at least a part of the heat source is associated with a heat sink to dissipate heat generated by the heat source;
- an enclosure having a plurality of portions with a first portion of the plurality of portions being at least partially transparent and one of the plurality of portions including a fluid transfer conduit interface, wherein the solid-state light source is mounted within the plurality of portions to form two sections of the enclosure that are separated from one another, the LEDs are located in the first section facing the first portion of the enclosure that is at least partially transparent and the heat sink is located in the second section of the enclosure; and
- a fluid transfer conduit connected to the enclosure via the fluid transfer conduit interface to allow fluid to transport heat generated by the heat source away from the heat sink of the solid-state light source;
- wherein the solid-state light source is mounted in a building structure, the fluid transfer conduit is in fluid communication with an outside of the building structure at one end and in fluid communication with the enclosure at another end, and wherein connected to the fluid conduit is a fan for moving fluid through the enclosure, through the fluid transfer conduit, and to the outside of the building.

* * * * *